(12) United States Patent  
Stepkowski et al.

(10) Patent No.: US 9,018,006 B2  
(45) Date of Patent: Apr. 28, 2015

(54) STABLE TREGS AND RELATED MATERIALS AND METHODS

(75) Inventors: Stanislaw M. Stepkowski, Sylvania, OH (US); Wenhao Chen, Toledo, OH (US); Yoshihiro Miyahara, Toledo, OH (US)

(73) Assignee: The University of Toledo, Toledo, OH (US)

( * ) Notice: Subject to any disclaimer, the term of this patent is extended or adjusted under 35 U.S.C. 154(b) by 96 days.

(21) Appl. No.: 13/811,778

(22) PCT Filed: Jul. 25, 2011

(86) PCT No.: PCT/US2011/045036  
§ 371 (c)(1),  
(2), (4) Date: Jul. 5, 2013

(87) PCT Pub. No.: WO2012/012737  
PCT Pub. Date: Jan. 26, 2012

(65) Prior Publication Data  
US 2013/0280208 A1  Oct. 24, 2013

Related U.S. Application Data

(60) Provisional application No. 61/367,347, filed on Jul. 23, 2010.

(51) Int. Cl.  
*C12N 5/0783* (2010.01)  
*C07K 16/28* (2006.01)  
*A61K 39/00* (2006.01)

(52) U.S. Cl.  
CPC .......... *C12N 5/0637* (2013.01); *A61K 2039/505* (2013.01); *A61K 2039/507* (2013.01); *C07K 16/2809* (2013.01); *C07K 16/2845* (2013.01); *C07K 2317/73* (2013.01); *C07K 2317/74* (2013.01); *C12N 5/0636* (2013.01); *C12N 2501/2302* (2013.01); *C12N 2501/2325* (2013.01); *C12N 2501/51* (2013.01); *C12N 2501/515* (2013.01); *C12N 2501/599* (2013.01); *C12N 2501/727* (2013.01); *A61K 35/17* (2013.01)

(58) Field of Classification Search  
CPC combination set(s) only.  
See application file for complete search history.

(56) References Cited

U.S. PATENT DOCUMENTS

| | | | |
|---|---|---|---|
| 4,603,137 A | 7/1986 | Bhat et al. | |
| 5,474,771 A | 12/1995 | Lederman et al. | |
| 5,547,852 A | 8/1996 | Seiler et al. | |
| 5,672,687 A | 9/1997 | Hermentin et al. | |
| 5,885,573 A | 3/1999 | Bluestone et al. | |
| 5,908,925 A | 6/1999 | Cohen et al. | |
| 5,993,816 A | 11/1999 | Lederman et al. | |
| 6,113,901 A | 9/2000 | Bluestone | |
| 6,143,297 A | 11/2000 | Bluestone | |
| 6,210,661 B1 | 4/2001 | Enssle et al. | |
| 6,294,172 B1 | 9/2001 | Bosslet et al. | |
| 6,328,954 B1 | 12/2001 | Enssle et al. | |
| 6,331,433 B1 | 12/2001 | Lederman et al. | |
| 6,331,615 B1 | 12/2001 | Lederman et al. | |
| 6,403,091 B1 | 6/2002 | Lederman et al. | |
| 6,406,696 B1 | 6/2002 | Bluestone | |
| 6,451,310 B1 | 9/2002 | Lederman et al. | |
| 6,455,044 B1 | 9/2002 | Lederman et al. | |
| 6,475,717 B1 | 11/2002 | Enssle et al. | |
| 6,491,916 B1 | 12/2002 | Bluestone et al. | |
| 6,592,868 B1 | 7/2003 | Lederman et al. | |
| 6,610,294 B1 | 8/2003 | Lederman et al. | |
| 6,793,924 B2 | 9/2004 | Lederman et al. | |
| 7,060,495 B2 | 6/2006 | Gehrmann et al. | |
| 7,070,777 B1 | 7/2006 | Lederman et al. | |
| 7,273,727 B2 | 9/2007 | Gehrmann et al. | |
| 7,722,862 B2 | 5/2010 | Bluestone et al. | |
| 7,754,482 B2 * | 7/2010 | Riley et al. | 435/375 |
| 8,323,969 B2 * | 12/2012 | Benedict et al. | 435/372.3 |
| 8,748,464 B2 * | 6/2014 | Verdin et al. | 514/366 |
| 2001/0051373 A1 | 12/2001 | Saha | |
| 2003/0232738 A1 | 12/2003 | Finkel et al. | |
| 2004/0132161 A1 | 7/2004 | Finkel et al. | |
| 2005/0124645 A1 | 6/2005 | Finkel | |
| 2005/0186207 A1 | 8/2005 | Bluestone et al. | |
| 2005/0203177 A1 | 9/2005 | Kirken et al. | |
| 2006/0002933 A1 | 1/2006 | Bluestone et al. | |
| 2006/0110392 A1 | 5/2006 | Lederman et al. | |
| 2006/0115899 A1 | 6/2006 | Buckner et al. | |
| 2006/0233751 A1 | 10/2006 | Bluestone et al. | |
| 2006/0292142 A1 | 12/2006 | Bluestone et al. | |
| 2007/0190045 A1 | 8/2007 | Herold et al. | |
| 2007/0190052 A1 | 8/2007 | Herold et al. | |

(Continued)

OTHER PUBLICATIONS

Selvaraj et al., Journal of Immunology Jul. 15, 2007 vol. 179 No. 2 1390.*

(Continued)

*Primary Examiner* — Daniel C Gamett  
(74) *Attorney, Agent, or Firm* — MacMillan, Sobanski & Todd, LLC

(57) ABSTRACT

The present invention provides materials and methods related to culturing stable Treg cells or in vivo expansion of stable Treg cells, the cells made by the methods, treatments for various inflammatory/autoimmune pathologies and transplant/graft rejection, and related materials. Ex vivo induction and expansion of the stable Tregs is described, including use of inducing compositions, such as certain mAbs and other compounds, along with expansion medium comprising IL-2. In vivo expansion of stable Treg cells and treatments for various inflammatory/autoimmune pathologies and transplant/graft rejection are described, including the use of mAbs and their variants.

3 Claims, 23 Drawing Sheets

(56) References Cited

U.S. PATENT DOCUMENTS

| | | | |
|---|---|---|---|
| 2008/0131445 | A1 | 6/2008 | Bluestone et al. |
| 2008/0167220 | A1 | 7/2008 | Kirken et al. |
| 2009/0162334 | A1 | 6/2009 | Feng et al. |
| 2009/0196887 | A1 | 8/2009 | Morita et al. |
| 2009/0220528 | A1* | 9/2009 | Turka et al. ............... 424/173.1 |
| 2010/0003271 | A1 | 1/2010 | Stepkowski |
| 2010/0310588 | A1 | 12/2010 | Bluestone et al. |
| 2011/0076258 | A1* | 3/2011 | Grassi et al. ............... 424/93.71 |
| 2011/0150826 | A1* | 6/2011 | Paulsen et al. ............... 424/85.2 |
| 2013/0203080 | A1* | 8/2013 | Sitbon et al. ............... 435/7.23 |

OTHER PUBLICATIONS

Létourneau et al., Proc Natl Acad Sci U S A. Feb. 2, 2010;107(5):2171-2176.*

Lio, Immunity. Jan. 2008 ; 28(1): 100-111.*

Popmihajlov (2008) PLoS One 3(2): e1581. doi:10.1371/ journal.pone.0001581.*

Borst, et al., BMA031, a Monoclonal Antibody Suited to Identify the T-Cell Receptor αβ/CD3 Complex on Viable Human T Lymphocytes in Normal and Disease States, Human Immunology, 1990, vol. 29, pp. 175-188.

Freedman, et al., B7, a B-cell-restricted antigen that indentifies preactivated B cells, J. Immunology, 1987, 139, pp. 3260-3267, Abstract.

Graham, et al., An Immobile Subset of Plasma Membrane CD11b/CD18 (Mac-1) Is Involved in Phagocytosis of Targets Recognized by Multiple Receptors, The Journal of Immunology, 1989, vol. 142, pp. 2352-2358.

PCT International Search Report and the Written Opinion, PCT/US2011/045036, filed Jul. 25, 2011, dated Mar. 8, 2012.

Pfeffer, et al., A Scandinavian two-center study of BMA 031 in Steroid-Resistant Rejection of Renal Grafts, PubMed, 1993, Abstract.

Roncador, et al., Analysis of FOXP3 protein expression in human CD4•CD25• regulatory T cells at the single-cell level, Eur. J. Immunol., 2005, vol. 35, pp. 1681-1691.

Selvaraj, et al., A Kinetic and Dymanic Analysis of Foxp3 Induced in T Cells by TGF-$\beta^1$, The Journal of Immunology, 2007, 178, pp. 7667-7677.

Shearman, et al., Construction, Expression and Characterization of Humanized Antibodies Directed Against the Human α/β T Cell Receptor, The Journal of Immunology, 1991, vol. 147, pp. 4366-4373.

Tredget, et al., Monotherapy with anti-LFA-1 Monoclonal Antibody Promotes Long-Term Survival of Rat Islet Xenografts, Cell Transplant, 2008, vol. 17(6), pp. 599-608.

Walker, et al., Induction of FoxP3 and acquisition of T regulatory activity by stimulated human CD4•CD25•T cells, The Journal of Clinical Investigation, 2003, vol. 112, pp. 1437-1443.

Wang, et al., "Default" Generation of Neonatal Regulatory T Cells, The Journal of Immunology, 2010, vol. 185, pp. 71-78.

* cited by examiner

Two-phase culture conditions

STABLE TREGS AND RELATED MATERIALS AND METHODS

CROSS-REFERENCE TO RELATED APPLICATIONS

This is a national stage application filed under 37 CFR 1.371 of international application PCT/US2011/045036 filed Jul. 25, 2011, which claims the priority to U.S. Provisional Application Ser. No. 61/365,347 filed Jul. 23, 2010, the entire disclosures of which are expressly incorporated herein by reference.

STATEMENT REGARDING FEDERALLY SPONSORED RESEARCH

This invention was made with government support under NIH grant HL 69723, awarded by the National Institutes of Health. The government may have certain rights in this invention.

TECHNICAL FIELD

This invention relates generally to the field of cellular biology and biochemistry. More particularly, it concerns cell culture technology. Certain aspects of the invention include application in diagnostics and therapeutics, particularly those related to immune response.

BACKGROUND

The human immune system has a myriad of diverse T-cell clones, each contributing to the effective and optimal immune responses towards foreign- or self-antigens. If proper control of the "anti-self" immune response is not imposed and maintained, the resulted "anti-self" response leads to development of autoimmune diseases. While the vast majority of self-reactive T-cell clones is deleted in the thymus (negative selection), some remain self-responsive, thus creating self-attacking T effector cells. To counterbalance these problems, there is a specialized population of T-cells called regulatory T-cells (Tregs) able to suppress the activation and expansion of other T-cells to maintain a fine homeostatic balance between reactivity to foreign- and self-antigens. These Tregs are characterized by a high level expression of surface interleukin-2 receptor a chain (CD25) and an intracellular expression of a master switch transcription factor called forkhead box protein P3 (Foxp3). There are at least two important functional populations of Tregs, namely natural Tregs (nTregs) that are continuously derived from the thymus and induced Tregs (iTregs) that are converted from peripheral naive CD4$^+$ T-cells. Transforming growth factor-$\beta$ (TGF-$\beta$) modulates the expansion of nTregs and induces conversion of CD4$^+$CD25$^-$ naïve T cells into CD4$^+$CD25$^+$ iTregs both in vitro and in vivo. While TGF-$\beta$-induced conversion to iTregs was explored for the application as future therapy for autoimmune diseases, the method proved to be unreliable and producing unstable iTregs, easily losing both Foxp3 expression and suppressor function upon environmental change (no exogenous TGF-$\beta$) and after repeated re-stimulation.

In spite of considerable research into this technology, the previous solutions have proven unreliable. The present invention provides stable Tregs and related methods and compositions.

The T-cell receptor (TCR) that is made up of TCRα and TCRβ chains has an exquisite specificity for its peptide antigen presented by the major histocompatibility complex (MHC) expressed on antigen presenting cells (APCs). Engagement of the TCR by peptide/MHC ligand controls T-cell generation and function. In transplantation, an acute rejection is mainly mediated by direct recognition of donor allo-MHC on "passenger APCs," while chronic rejection by the processed allopeptides presented by host self-MHC. Great efforts have been devoted to study the peptide-MHC/TCR interaction (1) and associated fates of T-cells during clonal expansion followed by clonal contraction (2-4). Moreover, manipulation of TCR engagement by modification of peptide/antigen or TCR engineering have been explored for potential therapeutic applications (5-7).

Binding of surface receptors by monoclonal antibodies (mAbs) may result in the depletion of cells or in the agonistic/antagonistic effects mimicking/blocking the action of the receptor's natural ligands (8). The inventors have explored the therapeutic potential of a TCRβ chain-specific mAb (9). This is different from the first mAb approved for clinical application namely mouse anti-human CD3 agonist (OKT3 mAb). The OKT3 mAb targets the $\epsilon$ chain within the CD3$\epsilon\gamma$ or $\epsilon\delta$ dimers, which is implicated in the signaling of the TCR/CD3 complex (10;11). Initially, the OKT3 mAb was used as an effective agent to prevent the post-transplant acute rejection. Nevertheless, OKT3 mAb was shown to be a potent mitogenic agent for T-cells; almost immediately after administration, OKT3 mAb elicited the release of many cytokines causing flu-like symptoms in treated patients (12). To reduce such side effects, the FcR-non-binding humanized anti-CD3 mAbs (teplizumab) was developed (13). Because the Protégé Encore phase III clinical study with teplizumab was suspended for the lack of sufficient efficacy for type 1 diabetes (T1D) and other clinical trials with anti-CD3 mAb are still underway (14), its long-term therapeutic effects remain obscure. Thus, safer and more effective methods to modulate the TCR signal are still needed for induction of tolerance.

In 1994, the inventors applied a mouse anti-human TCR mAb (clone BMA 031) as an induction therapy for kidney transplant patients. Transient administration of BMA 031 mAb improved kidney allograft survival, and none of the treated patients showed even moderately adverse effects as seen in OKT3 mAb-treated patients (15). Later, another group also showed that a different anti-human TCR mAb (clone T10B9) provided treatment for allograft rejection as effective as that of OKT3 mAb with fewer untoward effects, namely less cytokine release and fewer serious infections (16). The inventors and other groups confirmed the effectiveness of anti-TCR mAbs in preventing skin allograft rejection (17), graft-versus-host disease (18), and in the synergistic interaction with cyclosporine to prolong rat heart allograft survivals (9). Recent clinical reports re-emphasized the importance of using antibodies for induction therapies not only to prevent initial acute rejection but also to promote long-term allograft survival (19). The aim of this study was to determine whether TCR-specific mAb has robust tolerogenic effects in models of organ allograft transplantation and for treating T1D. The inventors found that transient anti-TCRβ mAb therapy (clone H57-597) led to: 1) initial reduction of conventional T-cells number with enrichment of FoxP3-expressing Treg cells; 2) minimal cytokine production; 3) abrogation of antigen-specific T-cell responses; 4) protection against the onset of T1D; 5) remission of new onset T1D; and 6) induction of tolerogenic effects to heart allografts. The inventors' findings revealed that transient TCR modulation by anti-TCR mAb provides a potent therapeutic approach for induction of tolerance in T1D and in organ transplant models.

There is no admission that the background references disclosed in this section legally constitutes prior art.

SUMMARY OF THE INVENTION

The present invention is based on the following information and discoveries: The inventors have established new methods for induction and expansion of stable iTregs without addition of exogenous TGF-β. The methods are applied to produce ex vivo large quantities of stable iTregs. The stable iTregs may be used for research and/or in vivo therapy of patients with autoimmune diseases and for prevention of allograft rejection. The ex vivo methods comprise an induction phase and an expansion phase (see FIG. 1).

Provided are compositions of matter comprising at least one stable iTreg cell, wherein the cell is $CD4^+$, $CD25^+Foxp3/GFP^+$ and wherein the iTreg cell is stable as defined. Particularly provided are those compositions wherein the at least one stable iTreg cell is stable for at least a number of generations selected from a group consisting of: two, three, four, five, and six. Particularly provided are those compositions wherein the cell is capable of expressing Foxp3 for at least six generations, or maintains Foxp3 expression and suppressive function upon activation. More particularly provided are those compositions, wherein at least one cell is at least a suitable number of cells for therapeutic use. Also particularly provided are those compositions which further comprise an adjuvant selected from the group consisting of: iTreg; anti-inflammatory; interleukin, interferon; and cytokine. Cells made by any process herein are also provided, as are pharmaceutical preparations comprising cells herein, including those which further comprise an adjuvant. Also provided are kits comprising a cell made by a process herein.

Method 1

Provided herein are methods to make stable iTreg cells, comprising introducing an inducer composition to an inducible first cell culture, wherein the inducer composition comprises anti-CD3 mAb/anti-CD28 mAb and at least one composition selected from the group consisting of: anti-IL-2 mAb; anti-CD25 mAb; or Janus tyrosine kinase (Jak3) inhibitor, and wherein the first cell culture comprises $CD4^+$ $Foxp3/GFP^-$ cells in a medium with or without syngeneic antigen presenting cells.

Also provided herein are methods to make stable iTreg cells, comprising: introducing an inducer composition to an inducible first cell culture, wherein the inducer composition comprises anti-CD3 mAb/anti-CD28 mAb and 0 to 10 μg/ml anti-IL-2, 0 to 10 μg/ml anti-CD25 mAb, and 50 to 150 nM Janus tyrosine kinase (Jak3) inhibitor; and wherein the first cell culture comprises $CD4^+$ $Foxp3/GFP^-$ cells in a medium with or without syngeneic antigen presenting cells (APC).

Also provided herein are methods to make stable iTreg cells, comprising: introducing an inducer composition to an inducible first cell culture, wherein the inducer composition comprises anti-CD3 mAb/anti-CD28 mAb and 5 μg/ml anti-IL-2, 5 μg/ml antiCD25 MAb, and 100 nM Janus tyrosine kinase (Jak3) inhibitor; and wherein the cell culture comprises $CD4^+$ $Foxp3/GFP^-$ cells in a medium with or without syngeneic antigen presenting cells.

Method 2

Also provided herein are methods to make stable Treg cells, comprising introducing an inducer composition to an inducible first cell culture, wherein the inducer composition comprises TCRβ mAb, and wherein the first cell culture comprises $CD4^+$ $Foxp3/GFP^-$ cells in a medium with irradiated syngeneic cells.

Also provided herein are methods to make stable Treg cells, comprising: introducing an inducer composition to an inducible first cell culture, wherein the inducer composition comprises 0.5 to 10 μg/ml of anti-TCRβ mAb wherein the first cell culture comprises $CD4^+$ $Foxp3/GFP^-$ cells in a medium with 20 Gray irradiated spleen cells.

Method 3

Also provided herein are methods to make stable Treg cells, comprising introducing an inducer composition to an inducible first cell culture, wherein the inducer composition comprises anti-CD3 mAb/anti-CD11a mAb, and wherein the first cell culture comprises $CD4+Foxp3/GFP^-$ cells in a medium with syngeneic antigen presenting cells.

Also provided herein are methods to induce stable Treg cells, comprising: introducing an inducer composition to an inducible first cell culture, wherein the inducer composition comprises anti-CD3 mAb and 0.5-15 μg/ml anti-CD11a mAb, and wherein the first cell culture comprises $CD4^+$ $Foxp3/GFP^-$ cells in a medium with syngeneic antigen presenting cells (APC).

Additional Methods

Also provided herein are two-phase methods of obtaining a stable regulatory T cell, comprising a first induction phase and a second expansion phase, wherein the induction phase comprises contacting a naive CD4 T cell with a stimulatory signal and an appropriate amount of a combination of anti-IL-2 mAb, or anti-IL-2 receptor mAb, or Jak3 inhibitor, wherein the stimulatory signal is a combination of an anti-CD3 antibody and an anti-CD28 antibody, and wherein the Foxp3 induction phase comprises replacing the medium from the conditioning phase with a fresh culture medium containing an appropriate amount of IL-2 and without addition of factors used in conditioning phase; and wherein the generated regulatory T cell expresses forkhead box P3 (Foxp3) transcription factor, a GITR marker, a CTLA4 marker, a CD25 marker, and suppresses at least 80% proliferation of an effector T cell in a in vitro suppressor assay at the 1:1 ratio.

Also provided herein are two-phase methods of obtaining a stable regulatory T cell comprising a first induction phase and a second expansion phase, wherein the induction phase comprises contacting a naive CD4 T cell with a stimulatory signal and an appropriate amount of an anti-T cell receptor-β (TCRβ) mAb, wherein the stimulatory signal is a combination of an anti-CD3 antibody and an anti-CD28 antibody, and wherein the expansion phase comprises replacing the medium from the induction phase with a fresh culture medium containing an appropriate amount of IL-2 without addition of factors used in the induction phase; and wherein the generated regulatory T cell expresses Foxp3 transcription factor, a GITR marker, a CTLA4 marker, a CD25 marker, and suppresses at least 80% proliferation of an effector T cell in a in vitro suppressor assay at the 1:1 ratio.

Also provided herein are two-phase methods of obtaining a stable regulatory T cell comprising a first induction phase and a second expansion phase, wherein the induction phase comprises a naive CD4 T cell with a stimulatory signal and an appropriate amount of an anti-CD11a MAb, wherein the stimulatory signal is a combination of an anti-CD3 antibody and an anti-CD28 antibody, and wherein the expansion phase comprises replacing the medium from the induction phase with a fresh culture medium containing an appropriate amount of IL-2 without addition of factors used in induction phase; and the generated regulatory T cell expresses Foxp3 transcription factor, a GITR marker, a CTLA4 marker, a CD25 marker, and suppresses at least 80% proliferation of an effector T cell in a in vitro suppressor assay at the 1:1 ratio.

Also provided are any method above, wherein: the method is in vitro; and/or wherein culturing is accomplished in the absence of TGF-β; and/or wherein: a) the response is a pathology inducing response; or b) the contacting occurs in the presence of at least two of the neutralizing antibodies;

and/or which further comprises a step of culturing the inducer composition and inducible first cell culture for at least: 2 to 4 days so as to produce a second cell culture; and/or which further comprises a step of washing the second cell culture; and/or which further comprises a step of introducing IL-2 supplemented medium to the second cell culture; and/or wherein the concentration of IL-2 is 1 to 25 units/ml of medium; and/or wherein the concentration of IL-2 is 10 units/ml of medium; and/or which further comprises culturing the medium and second cell culture for at least 2 to 4 days an additional three days so as to produce a third cell culture; and/or wherein the Jak3 inhibitor is CP 690,550; and/or wherein the IL-2 is recombinant; and/or wherein the CD4$^+$ Foxp3/GFP$^-$ cells are mammalian T cells; and/or wherein the resulting Foxp3/GFP$^+$ cells remain Foxp3/GFP$^+$ for at least six generations, or maintain Foxp3 expression and suppressive function upon activation.

Treatments

Also provided are methods to treat autoimmune disease in patient in need of such treatment, comprising administering a pharmaceutically-effective amount of a composition herein. Particularly provided are those methods wherein the autoimmune disease is selected from the group consisting of: ankylosing spondylitis; Chagas disease; chronic obstructive pulmonary disease; Crohns Disease; idiopathic inflammatory bowel disease; dermatomyositis; diabetes mellitus type 1; endometriosis; Goodpasture's syndrome; Graves' disease; Guillain-Barré syndrome (GBS); Hashimoto's disease; hidradenitis suppurativa; kawasaki disease; IgA nephropathy; idiopathic thrombocytopenic purpura; interstitial cystitis; lupus erythematosus; mixed connective tissue disease; morphea; multiple sclerosis; myasthenia gravis; narcolepsy; neuromyotonia; pemphigus vulgaris; pernicious anemia; psoriasis; psoriatic arthritis; polymyositis; polymyalgia rheumatica; primary biliary cirrhosis; relapsing polychondritis; rheumatoid arthritis; schizophrenia; scleroderma; sclerosing colangitis; Sjögren's syndrome; stiff person syndrome; temporal arteritis; ulcerative colitis; vasculitis Vitiligo; Wegener's granulomatosis. Also particularly provided are such methods which further comprise administering an adjuvant.

Also provided herein are methods to ameliorate transplant rejection, comprising administering a composition herein. Particularly provided are such methods wherein the transplant is selected from the group consisting of: graft, partial organ transplant; and full organ transplant.

Also provided are methods to reduce the risk of adhesions after a surgical procedure in a surgical patient in need of risk reduction, comprising administering a composition herein.

Also provided are methods to reduce the risk of neurological, vascular or muscle tissue impairment after a surgical procedure in a surgical patient in need of risk reduction, comprising administering a composition herein.

Also provided are methods to ameliorate inflammation in a patient in need of inflammation amelioration, comprising administering a composition herein. Particularly provided are such methods, wherein the patient suffers from a condition selected from the group consisting of: stroke, vascular disease, cancer, sepsis, fever, injury, burn, toxin exposure, infection, radiation, poisoning, and allergic reaction.

In Vivo Methods

Also provided are methods for downmodulating an immune response in a subject comprising administering to the subject an anti-TCRβ antibody.

Preferred are those methods:
wherein the anti-TCRβ antibody is H57-597 or TCRβ-inhibiting H57-597 structural variant; wherein the immune response is an autoimmune disorder;

wherein the immune disorder is selected from the group consisting of: ankylosing spondylitis; chagas disease; chronic obstructive pulmonary disease; Crohns disease; idiopathic inflammatory bowel disease; dermatomyositis; diabetes mellitus type 1; endometriosis; Goodpasture's syndrome; Graves' disease; Guillain-Barré syndrome (GBS); Hashimoto's disease; hidradenitis suppurativa; Kawasaki disease; IgA nephropathy; idiopathic thrombocytopenic purpura; interstitial cystitis; lupus erythematosus; mixed connective tissue disease; morphea; multiple sclerosis; myasthenia gravis; narcolepsy; neuromyotonia; pemphigus vulgaris; pernicious anemia; psoriasis; psoriatic arthritis; polymyositis; polymyalgia rheumatica; primary biliary cirrhosis; relapsing polychondritis; rheumatoid arthritis; schizophrenia; scleroderma; sclerosing colangitis; Sjögren's syndrome; stiff person syndrome; temporal arteritis; ulcerative colitis; vasculitis vitiligo; Wegener's granulomatosis;

wherein the immune response is host versus graft response; wherein the host versus graft response is due to a transplant;

wherein the transplant is selected from the group consisting of: heart; lung; liver; kidney; intestine; eye; skin; bone; cells; body fluid; blood; digit; muscle; tendon; and ligament;

wherein the anti-TCRβ antibody is administered to the subject prior to, simultaneously with, or within 150 hours of a transplant procedure;

wherein the anti-TCRβ antibody is administered to the subject within 72 hours of a transplant procedure;

wherein the anti-TCRβ antibody is administered in 3 to 10 doses;

wherein the anti-TCRβ antibody is administered in 5 to 7 doses;

and/or which further comprises administering anti-CD11a antibody, preferably mAb LFA-1.

Also provided are methods to reduce T-cell numbers in vivo, comprising administering anti-TCRβ antibody, preferably H57-597 to a mammal.

Also provided are methods to enrich Treg cells in vivo, comprising administering anti-TCRβ antibody, preferably H57-597 to a mammal.

Also provided are methods to arrest T-cell response to antigen in vivo, comprising administering anti-TCRβ antibody, preferably H57-597 to a mammal.

Also provided are methods to reduce cytokine production in vivo, comprising administering anti-TCRβ antibody, preferably H57-597 to a mammal.

Also provided are methods to enrich Treg cells in vitro, comprising introducing anti-TCRβ antibody, preferably H57-597 to an in vitro cell culture.

Also provided are methods to identify test compounds useful to enrich Treg cells, comprising comparing a test compound's ability to enrich Treg cells with anti-TCRβ antibody, preferably H57-597 ability to enrich Treg cells, and identifying compounds useful to enrich Treg cells based on relative ability to enrich Treg cells.

Also provided are methods to identify test compounds useful to modulate immune response, comprising comparing a test compound's ability to modulate immune response with anti-TCRβ antibody, preferably H57-597 ability to modulate immune response, and identifying compounds useful to modulate immune response based on relative ability to modulate immune response.

Preferred are those methods:
wherein the immune response is selected from the group consisting of: ankylosing spondylitis; chagas disease; chronic obstructive pulmonary disease; Crohns disease; idiopathic inflammatory bowel disease; dermatomyositis; diabetes mellitus type 1; endometriosis; Goodpasture's syndrome;

Graves' disease; Guillain-Barré syndrome (GBS); Hashimoto's disease; hidradenitis suppurativa; Kawasaki disease; IgA nephropathy; idiopathic thrombocytopenic purpura; interstitial cystitis; lupus erythematosus; mixed connective tissue disease; morphea; multiple sclerosis; myasthenia gravis; narcolepsy; neuromyotonia; pemphigus vulgaris; pernicious anemia; psoriasis; psoriatic arthritis; polymyositis; polymyalgia rheumatica; primary biliary cirrhosis; relapsing polychondritis; rheumatoid arthritis; schizophrenia; scleroderma; sclerosing colangitis; Sjögren's syndrome; stiff person syndrome; temporal arteritis; ulcerative colitis; vasculitis vitiligo; Wegener's granulomatosis.

Also provided are methods to identify test compounds useful to prevent Type 1 diabetes, comprising comparing a test compound's ability to enrich Treg cells with anti-TCRβ antibody, preferably H57-597 ability to enrich Treg cells, and identifying compounds useful to prevent Type 1 diabetes based on relative ability to enrich Treg cells.

Also provided are methods to identify test compounds useful to treat Type 1 diabetes, comprising comparing a test compound's ability to enrich Treg cells with anti-TCRβ antibody, preferably H57-597 ability to enrich Treg cells, and identifying compounds useful to treat Type 1 diabetes based on relative ability to enrich Treg cells.

Also provided are methods to identify test compounds useful to modulate host/graft response, comprising comparing a test compound's ability to enrich Treg cells with anti-TCRβ antibody, preferably H57-597 ability to enrich Treg cells, and identifying compounds useful to modulate host/graft based on relative ability to enrich Treg cells.

Preferred are those methods:
wherein the host/graft response is a human host and human transplant tissue;
wherein the human transplant tissue is selected from the group consisting of: heart; lung; liver; kidney; intestine; eye; skin; bone; cells; body fluid; blood; digit; muscle; tendon; and ligament.

Also provided are methods for downmodulating an immune response in a subject comprising administering to the subject an anti-CD11a antibody.

Preferred are those methods:
wherein the anti-CD11a antibody is LFA-1 or CD11a-inhibiting LFA-1 structural variant;
wherein the immune response is an autoimmune disorder;
wherein the immune disorder is selected from the group consisting of: ankylosing spondylitis; chagas disease; chronic obstructive pulmonary disease; Crohns disease; idiopathic inflammatory bowel disease; dermatomyositis; diabetes mellitus type 1; endometriosis; Goodpasture's syndrome; Graves' disease; Guillain-Barré syndrome (GBS); Hashimoto's disease; hidradenitis suppurativa; Kawasaki disease; IgA nephropathy; idiopathic thrombocytopenic purpura; interstitial cystitis; lupus erythematosus; mixed connective tissue disease; morphea; multiple sclerosis; myasthenia gravis; narcolepsy; neuromyotonia; pemphigus vulgaris; pernicious anemia; psoriasis; psoriatic arthritis; polymyositis; polymyalgia rheumatica; primary biliary cirrhosis; relapsing polychondritis; rheumatoid arthritis; schizophrenia; scleroderma; sclerosing colangitis; Sjögren's syndrome; stiff person syndrome; temporal arteritis; ulcerative colitis; vasculitis vitiligo; Wegener's granulomatosis;
wherein the immune response is host versus graft response;
wherein the host versus graft response is due to a transplant;
wherein the transplant is selected from the group consisting of: heart; lung; liver; kidney; intestine; eye; skin; bone; cells; body fluid; blood; digit; muscle; tendon; and ligament;

wherein the anti-CD11a antibody is administered to the subject prior to, simultaneously with, or within 150 hours of a transplant procedure;
wherein the anti-CD11a antibody is administered to the subject within 72 hours of a transplant procedure;
wherein the anti-CD11a antibody is administered in 3 to 10 doses;
wherein the anti-CD11a antibody is administered in 5 to 7 doses; which further comprises administering anti-TCRβ antibody, preferably H57-597.

Also provided are methods to reduce T-cell numbers in vivo, comprising administering mAb LFA-1 to a mammal.

Also provided are methods to enrich Treg cells in vivo, comprising administering mAb LFA-1 to a mammal.

Also provided are methods to arrest T-cell response to antigen in vivo, comprising administering mAb LFA-1 to a mammal.

Also provided are methods to reduce cytokine production in vivo, comprising administering mAb LFA-1 to a mammal.

Also provided are methods to enrich Treg cells in vitro, comprising introducing mAb LFA-1 to an in vitro cell culture.

Also provided are methods to identify test compounds useful to enrich Treg cells, comprising comparing a test compound's ability to enrich Treg cells with mAb LFA-1 ability to enrich Treg cells, and identifying compounds useful to enrich Treg cells based on relative ability to enrich Treg cells.

Also provided are methods to identify test compounds useful to modulate immune response, comprising comparing a test compound's ability to modulate immune response with mAb LFA-1 ability to modulate immune response, and identifying compounds useful to modulate immune response based on relative ability to modulate immune response.

Preferred are those methods:
wherein the immune response is selected from the group consisting of: ankylosing spondylitis; chagas disease; chronic obstructive pulmonary disease; Crohns disease; idiopathic inflammatory bowel disease; dermatomyositis; diabetes mellitus type 1; endometriosis; Goodpasture's syndrome; Graves' disease; Guillain-Barré syndrome (GBS); Hashimoto's disease; hidradenitis suppurativa; Kawasaki disease; IgA nephropathy; idiopathic thrombocytopenic purpura; interstitial cystitis; lupus erythematosus; mixed connective tissue disease; morphea; multiple sclerosis; myasthenia gravis; narcolepsy; neuromyotonia; pemphigus vulgaris; pernicious anemia; psoriasis; psoriatic arthritis; polymyositis; polymyalgia rheumatica; primary biliary cirrhosis; relapsing polychondritis; rheumatoid arthritis; schizophrenia; scleroderma; sclerosing colangitis; Sjögren's syndrome; stiff person syndrome; temporal arteritis; ulcerative colitis; vasculitis vitiligo; Wegener's granulomatosis;

Also provided are methods to identify test compounds useful to prevent Type 1 diabetes, comprising comparing a test compound's ability to enrich Treg cells with mAb LFA-1 ability to enrich Treg cells, and identifying compounds useful to prevent Type 1 diabetes based on relative ability to enrich Treg cells.

Also provided are methods to identify test compounds useful to treat Type 1 diabetes, comprising comparing a test compound's ability to enrich Treg cells with mAb LFA-1 ability to enrich Treg cells, and identifying compounds useful to treat Type 1 diabetes based on relative ability to enrich Treg cells.

Also provided are methods to identify test compounds useful to modulate host/graft response, comprising comparing a test compound's ability to enrich Treg cells with mAb LFA-1 ability to enrich Treg cells, and identifying compounds useful to modulate host/graft based on relative ability to enrich Treg cells.

Preferred are those methods:
wherein the host/graft response is a human host and human transplant tissue;
wherein the human transplant tissue is selected from the group consisting of: heart; lung; liver; kidney; intestine; eye; skin; bone; cells; body fluid; blood; digit; muscle; tendon; and ligament.

Various objects and advantages of this invention will become apparent to those skilled in the art from the following detailed description of the preferred embodiment, when read in light of the accompanying figures.

BRIEF DESCRIPTION OF THE FIGURES

FIG. 2A. Naïve mouse CD4$^+$Foxp3/GFP$^-$ cells ($1\times10^6$/ml) cultured in a medium were stimulated with anti-CD3 mAb/anti-CD28 mAb in the presence of 5 µg/ml anti-IL-2 mAb, 5 µg/ml anti-CD25 mAb, or 100 nM Janus tyrosine kinase (Jak3) inhibitor (CP-690,550) for 3 days (induction phase). After washing, fresh medium was supplemented with 10 units/ml rIL-2 and cultured for additional 3 days (expansion phase). FACscan analysis of CD4$^+$Foxp3/GFP$^+$ cells was performed.

FIG. 2B. Cultures as in FIG. 2A were exposed to 100 ng/ml Stat5 inhibitor for the first 3 days, washed and cultured for remaining 3 days with rIL-2.

FIG. 2C. Following cultures with CP-690,550 as in A, washed cells were cultured with rIL-2 and examined by FACS on days 3, 4, 5 and 6 (n=3).

Whole splenocytes isolated from OT-I mice were CFSE-labeled and cultured in 96 well round bottom plates at a concentration of 2×10$^5$ cells/well. Histograms represent the CFSE fluorescence intensity within the CFSE$^+$ cell population after 3 days of culture in the presence of (i) 5 μg/mL Isotype Ab; (ii) 5 μg/mL H57-597 mAb; (iii) 5 μg/mL OVA$_{257-264}$ peptide; or (iv) 5 μg/mL H57-597 mAb plus 5 μg/mL OVA$_{257-264}$ peptide.

Figure 14A:
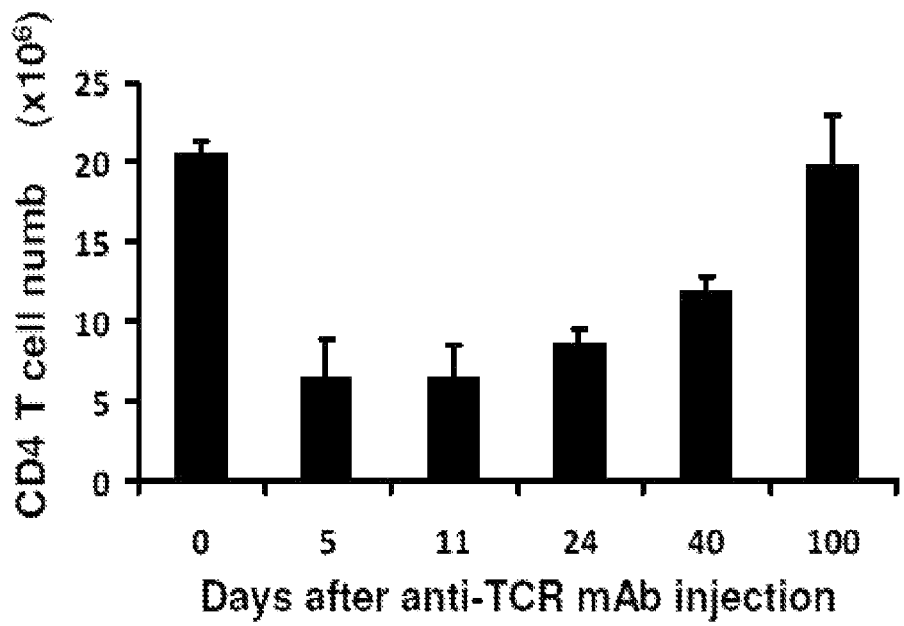
Figure 14B:
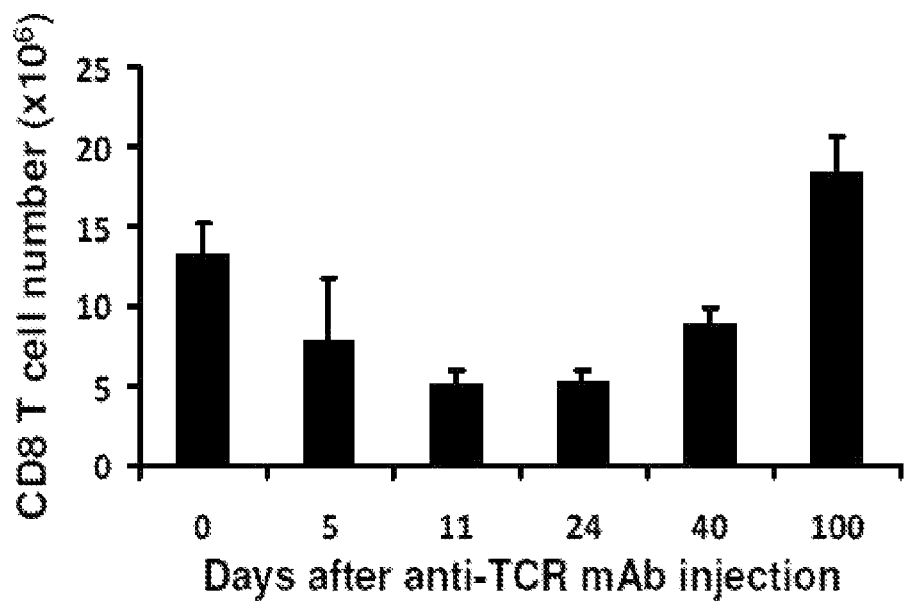

FIG. 14A-14B. Recovery of T-cell homeostasis in wild-type mice after treatment with H57-597 mAb.

Spleens from wild-type (B6) mice were harvested at the indicated days after i.p. injection with 1 mg/kg anti-TCR mAb (clone H57-597), and the total number of splenocytes was counted. (14A) Total CD4 T-cell numbers at different time points after treatment with anti-TCR mAb calculated from the frequency of CD4$^+$ cells by FACS analysis and the total number of splenocytes. (14B) Total CD8 T-cell numbers at different time points after treatment with anti-TCR mAb calculated as in (A). Each time point represents calculations from 3 different mice.

Figure 15A:
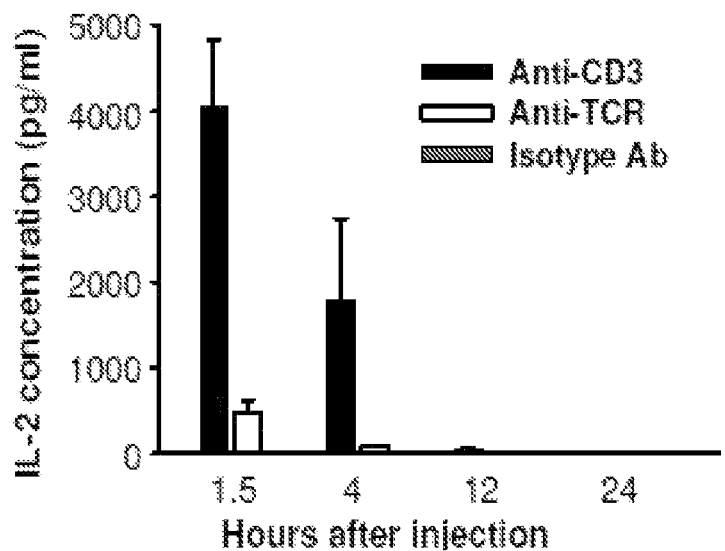
Figure 15B:
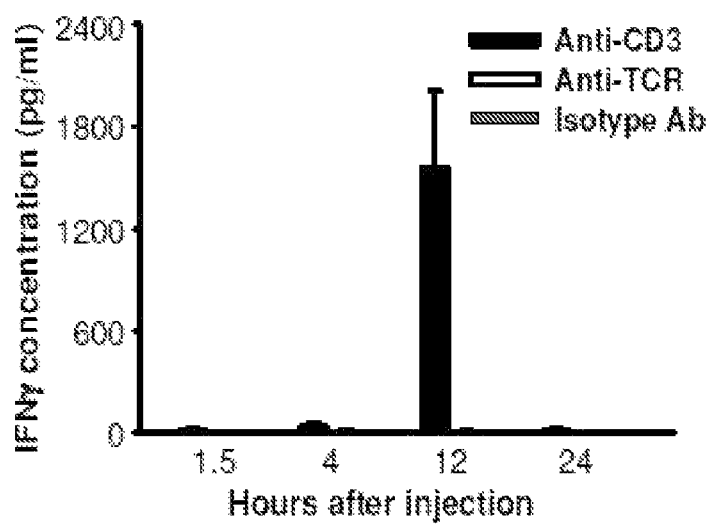
Figure 15C:
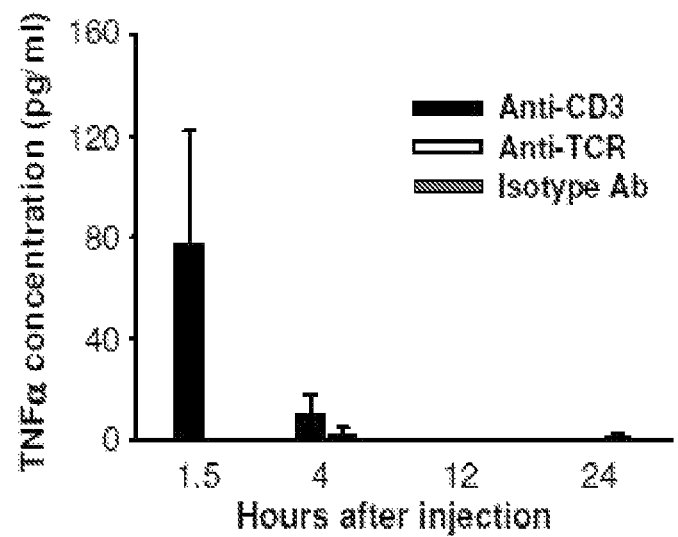
Figure 15D:
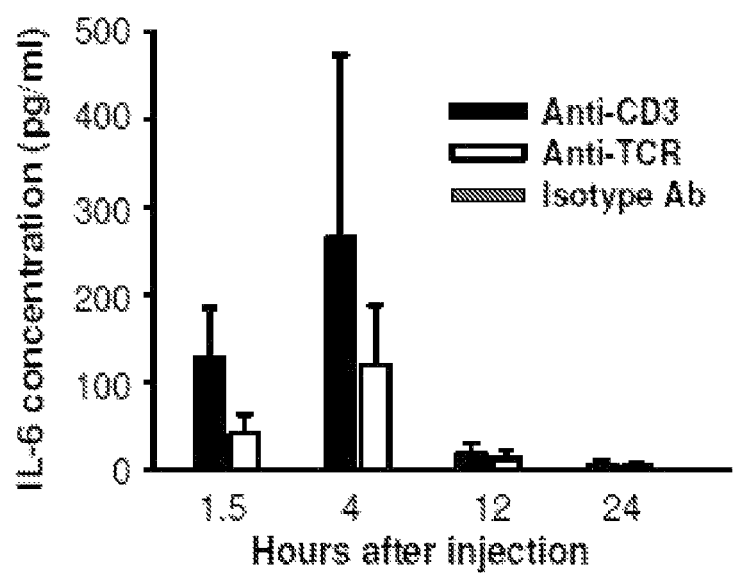

FIG. 15A-15B. Bio-Plex assay of cytokine production in wild-type mice after treatment with anti-TCR mAb, anti-CD3 mAb, or Isotype Ab.

Wild-type (B6) mice were injected with 1 mg/kg anti-CD3 mAb (clone 145-2C11), anti-TCR mAb (clone H57-597), or Isotype Ab. Mice were euthanized at the indicated hours after injection, and serum levels of (15A) IL-2; (15B) IFNγ; (15C) TNFα; and (15D) IL-6 were measured by Bio-Plex assay and shown in bar graphs. Each time point represents measurements from 3 mice.

Figure 16:
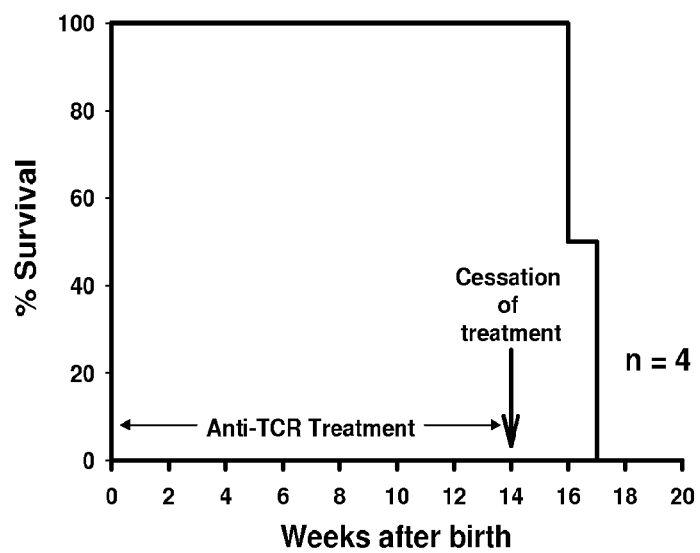

FIG. 16. Continuous treatment with anti-TCR mAb is required to maintain the survival of FoxP3$^{sf}$ mice. Male FoxP3$^{sf}$ mice were treated with 1 mg/kg per week after birth for 14 weeks. The genotype of FoxP3$^{sf}$ mice were confirmed at 4 weeks of age using genotyping PCR (according to Jackson Laboratories protocol). The graph shows survival of male FoxP3$^{sf}$ mice during and after cessation of treatment with anti-TCR mAb (n=4). Without treatment male FoxP3$^{sf}$ mice succumb to lethal autoimmune disease within 2 to 4 weeks of age (34).

The patent or application file may contain one or more drawings executed in color and/or one or more photographs. Copies of this patent or patent application publication with color drawing(s) and/or photograph(s) will be provided by the Patent Office upon request and payment of the necessary fee.

Figure 17:
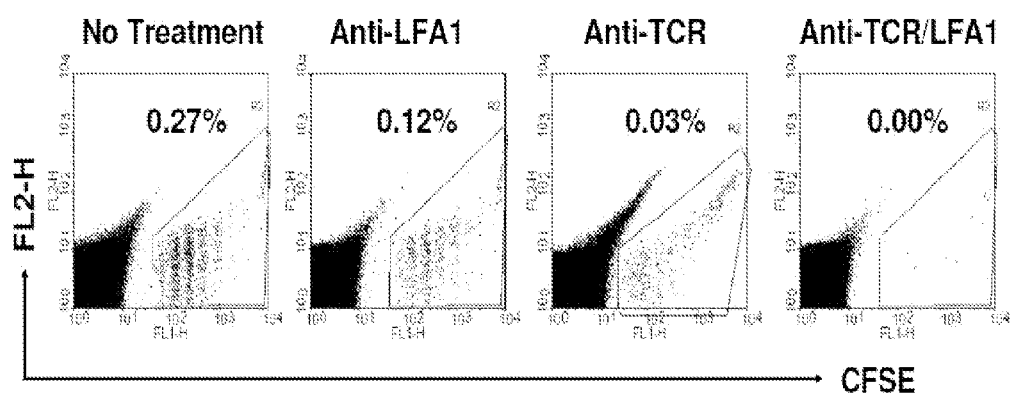

FIG. 17. Anti-TCRβ mAb combined with anti-CD11a (LFA-1) mAb induced complete elimination of T cells. To test the effect of two agents in vivo, normal B6 mice were injected with 1×10$^6$ CFSE-labeled splenocytes from OTII transgenic mice and injected with 5 μg ovalbumin (OVA) peptide and 1 mg/kg H57-597 mAb and 1 mg/kg anti-CD11a mAb alone or in combination. On day 3, mice showed that 0.27% CFSE-labeled T cells in controls were reduced to 0.12% by anti-LFA-1 mAb, to 0.03% by anti-TCR mAb and to 0.00% by two agents in combination (FIG. 17).

Figure 18:
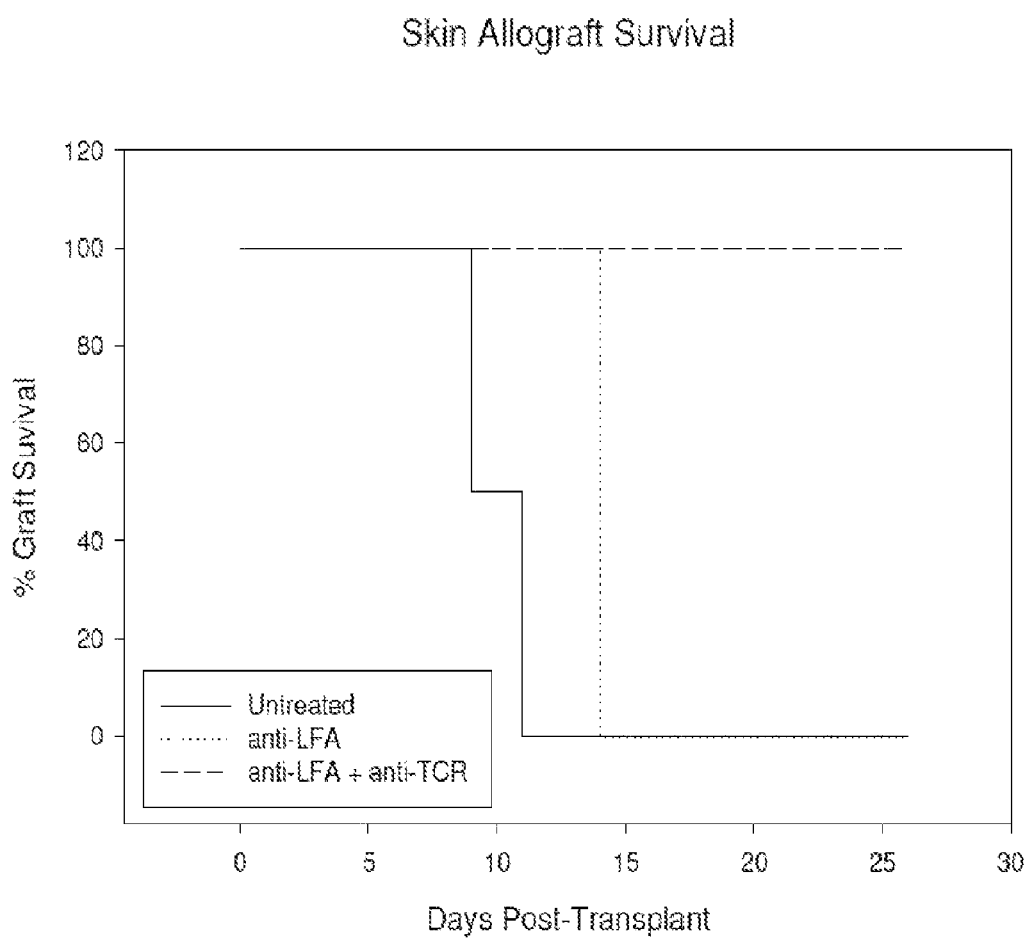

FIG. 18. Anti-TCRβ mAb combined with anti-LFA-1 mAb prolonged the survivals of skin allografts. To examine the tolerogenic effects, 1 mg/kg H57-597 mAb in combination with 1 mg/kg anti-CD11a mAb were injected (days 0, 1, 3, 7 and 11 post-grafting) into B6 recipients of Balb/c skin allografts. While untreated controls rejected skin allografts within 11 days (n=3), the therapy with anti-CD11a mAb alone slightly extended survivals to maximum 14 days (n=3). In contrast, the combination therapy prolonged survivals of skin allografts to more than 30 days, and all skin grafts remain surviving (FIG. 18; ongoing experiments).

DETAILED DESCRIPTION

The present invention is based in part on the discovery that modulation of the T-cell receptor (TCR) engagement with specific antigen-MHC complex may regulate T-cell responses against auto- and allo-antigens. Herein, the inventors found that in vivo administration of an anti-mouse TCRβ mAb (clone H57-597) resulted in a preferential reduction of antigen-reactive T-cells with enrichment of $CD4^+FoxP3^+$ Treg cells (~30% among $CD4^+$ cells). In contrast to an anti-CD3 mAb, administration of H57-597 mAb did not elicit production of high levels of TNF-α, IFN-γ, IL-2, and IL-6 cytokines. Strikingly, a single injection of H57-597 mAb into RIP-OVA$^{hi}$ mice completely inhibited the development of type 1 diabetes (T1D) that was induced by adoptively transferred OVA-specific T-cells. A short course of H57-597 mAb at 8 weeks of age prevented the development of T1D in normoglycemic NOD mice. Moreover, brief treatment with H57-597 mAb after onset of T1D induced remission in 6 out of 8 NOD mice. In a transplantation model, transient H57-597 mAb treatment alone produced long-term cardiac allograft survivals (>100 days; n=9). Adoptive transfer of tolerant splenocytes to syngeneic $Rag1^{-/-}$ recipients extended the survival of donor-specific but not third-party heart allografts. Thus, transient modulation of the TCRβ chain by H57-597 mAb during an ongoing immune response exhibits potent tolerogenic effects.

The results showed that transient TCR engagement with H57-597 mAb dramatically "reset" the T-cell composition, resulting in an initial reduction of conventional $CD4^+$ and $CD8^+$ T-cells with enrichment of $CD4^+FoxP3^+$ Treg cells. This reset period correlated with robust arrest of antigen-specific T-cell responses, as shown in SEB-treated mice and in RIP-OVA$^{hi}$ mice. Following the reset, long-term protection from T1D in NOD mice and long-term allograft survival correlated with the full recovery of $CD4^+$ and $CD8^+$ T-cell homeostasis. Moreover, the adoptive transfer from recipients that accepted heart allografts demonstrated that T-cell function was fully recovered against third-party alloantigens but remained hypo-responsive to donor alloantigens. This demonstrates that transient therapy with H57-597 mAb during initial exposure to donor alloantigens induced tolerogenic effects preferentially toward those alloantigens.

Despite extensive efforts, induction of complete and continuously maintained tolerance in T1D and in transplantation remains difficult while its mechanism elusive. The results suggest that at least two components may be necessary for successful immunomodulation to achieve tolerance, namely reduction of auto- or donor-reactive T-cells and elevation of negative regulatory mechanisms. The short therapy with anti-TCRβ mAb may proffer therapeutic potential with such dual roles for both transplantation and autoimmunity.

The present invention therefore provides materials and methods related to these new discoveries. In particular, compositions useful to treat such disorders as described herein, and as would be known to those skilled in the art. Also provided are methods to identify additional compositions useful to treat, methods to diagnose, methods to provide prognosis, methods to induce apoptosis, etc. Also provided are research tools associated with these discoveries, particularly kits and the like.

Specific objects of the present invention include:

Therapy with anti-T cell receptor (anti-TCR) monoclonal antibody (mAb) shortly prior and/or shortly after allograft transplantation increases the number of stable regulatory T cells.

Therapy with anti-TCR mAb shortly prior and/or shortly after allograft transplantation induces clonal deletion of antigen-reactive activated T cells.

Therapy with anti-TCR mAb shortly prior and/or shortly after allograft transplantation induces tolerogenic effect with long-term allograft survivals.

Short-term (5-7 doses) therapy with anti-TCR mAb prevents and blocks the onsets of type 1 diabetes.

Therapy with a combination of anti-TCR mAb and anti-CD11a mAb shortly prior and/or shortly after allograft transplantation increases the number of stable regulatory T cells.

Therapy with a combination of anti-TCR mAb and anti-CD11a mAb shortly prior and/or shortly after allograft transplantation induces clonal deletion of antigen-reactive activated T cells.

Therapy with a combination of anti-TCR mAb and anti-CD11a mAb shortly prior and/or shortly after allograft transplantation induces tolerogenic effect with long-term allograft survivals.

Short-term (5-7 doses) therapy with a combination of anti-TCR mAb and anti-CD11a mAb prevents and blocks the onsets of type 1 diabetes.

Therapy with 1-10 mg/kg anti-T cell receptor (anti-TCR) monoclonal antibody (mAb) shortly prior and/or shortly after (−7 to +14 days) allograft transplantation increases the number of stable regulatory T cells.

Therapy with 1-10 mg/kg anti-TCR mAb shortly prior and/or shortly after (−7 to +14 days) allograft transplantation induces clonal deletion of antigen-reactive activated T cells.

Therapy with 1-10 mg/kg anti-TCR mAb shortly prior and/or shortly after (−7 to +14 days) allograft transplantation induces tolerogenic effect with long-term allograft survivals.

Short-term (5-14 doses) therapy with 1-10 mg/kg anti-TCR mAb prevents and blocks the onsets of type 1 diabetes.

Therapy with a combination of 1-10 mg/kg anti-TCR mAb and 1-20 mg/kg anti-CD11a mAb shortly prior and/or shortly after allograft transplantation increases the number of stable regulatory T cells.

Therapy with a combination of 1-10 mg/kg anti-TCR mAb and 1-20 mg/kg anti-CD11a mAb shortly prior and/or shortly after allograft transplantation induces clonal deletion of antigen-reactive activated T cells.

Therapy with a combination of 1-10 mg/kg anti-TCR mAb and 1-20 mg/kg anti-CD11a mAb shortly prior and/or shortly after allograft transplantation induces tolerogenic effect with long-term allograft survivals.

Short-term (5-7 doses) therapy with a combination of 1-10 mg/kg anti-TCR mAb and 1-20 mg/kg anti-CD11a mAb prevents and blocks the onsets of type 1 diabetes.

The increased number of stable regulatory T cells, as defined by the elevation above regulatory T cell levels (CD4+CD25+Foxp3high) with suppressor function similar to the natural regulatory T cells.

Clonal deletion of antigen-reactive T cells as defined by the decreased number of antigen-reactive T cells.

Long-term allograft survival as defined by the survival more than 100 days without immunosuppressive therapy or with significantly reduced standard immunosuppressive therapy.

Prevention of type 1 diabetes as defined by therapy prior to an increased glucose levels.

Blocking the onset of type 1 diabetes as defined by effective therapy (lowering blood glucose levels; <200 mg/dL) in individual showing an elevated blood glucose levels (≥250 mg/dL).

DEFINITIONS AND ABBREVIATIONS

DNA—Deoxyribonucleic acid
iTreg Inducible regulatory T-cell (also known as adaptive regulatory T-cell or acquired regulatory T-cell)
mRNA Messenger RNA nTreg Natural regulatory T-cell (also known as innate regulatory T-cell)

PCR Polymerase chain reaction

RNA Ribonucleic acid

As used herein the term "treating" refers to preventing, suppressing, repressing or eliminating the disease or inflammatory condition. Preventing the disease or condition involves administering a composition of the present invention to a subject prior to onset of the disease. Suppressing the disease or condition involves administering a composition of the present invention to a subject after induction of the disease or condition but before its clinical appearance. Repressing a disease or condition involves administering a composition of the present invention to a subject after clinical appearance of the disease or condition.

As used herein, the expression "therapeutically effective amount" refers to an amount of the composition which is effective to achieve a desired therapeutic result, such as, for example, the prevention, amelioration or prophylaxis of an autoimmune disease or inflammatory condition.

As used herein, an "autoimmune disease" is a disease or disorder arising from and directed against an individual's own tissues. Examples of autoimmune diseases or disorders include, but are not limited to arthritis (rheumatoid arthritis, juvenile rheumatoid arthritis, psoriatic arthritis), conditions involving infiltration of T-cells and chronic inflammatory responses, autoimmune myocarditis, multiple sclerosis, pemphigus, and type 1 diabetes (also referred to as insulin-dependent diabetes mellitus (IDDM)).

As used herein, the term "organ or tissue transplant" refers to any solid organ such as kidneys, heart, lungs, liver, and pancreas including tissue grafts, and whole or selected populations of blood or bone marrow transplants.

Mammalian T-cells for use in the method of the invention may be isolated from a biological sample taken from a mammalian subject, such as a human subject, originating from a number of sources, including for example, peripheral blood mononuclear cells, bone marrow, thymus, tissue biopsy, tumor, lymph node tissue, gut associated lymphoid tissue, mucosa associated lymph node tissue, spleen tissue or any other lymphoid tissue and tumors. In a preferred embodiment, human T-cells are isolated as peripheral blood mononuclear cells (PBMC) from a blood sample obtained from the peripheral blood of a subject. T-cells may also be obtained from a unit of blood obtained from an apheresis or leukapheresis procedure.

Expansion Technique Creating Stable iTregs

A population of CD4+CD25− cells may be isolated from a sample comprising human T-cells through the use of gradients and positive/negative selection techniques well known to those of skill in the art. For example, PBMC can be partially purified by density gradient centrifugation (e.g., through a Ficoll-Hypaque gradient), by panning, affinity separation, cell sorting (e.g., using antibodies specific for one or more cell surface markers, such as anti-CD4 and anti-CD25 antibodies) and other techniques that provide enrichment of CD4+CD25− cells. An exemplary method for isolating CD4+CD25− cells is described in the Examples. After selection, the enriched CD4+CD25− cell population is preferably at least 95% CD25−, more preferably at least 99% CD25−, more preferably at least 99.9% CD25−, up to 100% CD25−.

Expansion Technique 2. Not Creating Stable iTregs.

In another embodiment, the method of this aspect of the invention further comprises the step of expanding the ex vivo generated Treg cell population. In accordance with this embodiment, T-Cell expansion may be accomplished by culturing the antigen-specific CD4+CD25+ Treg cells with a co-stimulatory agent comprising a CD3 activation and a CD28 activation for a time period sufficient to achieve the desired cell expansion. A number of anti-human CD3 monoclonal antibodies are commercially available, such as for example, OKT3, G19-4, Hit3a, and UCHT1 (Pharmigen, San Diego, Calif.). To further activate a population of T-cells, a co-stimulatory or accessory molecule on the surface of the T cells, such as CD28, is stimulated with a ligand that binds to the accessory molecule. Accordingly, one of skill in the art will recognize that any agent capable of cross-linking the CD28 molecules can be used to stimulate T cells, such as for example, an anti-CD28 antibody or a natural ligand for CD28. Exemplary anti-CD28 antibodies or fragments thereof include monoclonal antibody 93 (IgG2; Bristol Myers Squibb, Princeton, N.J.), monoclonal antibody KOLT-2 (IgG1), and CD28.2 (Pharmigen, San Diego, Calif.). Exemplary natural ligands include the B7 family of proteins such as B7-1 (CD80) and B7-2 (CD86) (Freedman et al., J. Immunol. 137:3260-3267 (1987)). In certain embodiments, the molecule providing the activation signal, such as a CD3 ligand, and the co-stimulatory molecule, such as a CD28 ligand, are coupled to the same surface, such as a particle or bead. One, two, or more, stimulatory molecules may be attached to the same particle or bead.

The ex vivo generated iTreg cells are expanded in culture for a time period ranging from about 6 days to about 14 days. In certain embodiments, the expansion obtained is in the range of from about 10 fold to about 50 fold or higher. The expanded Treg population may be assayed for particular Treg characteristics, such as, for example, CD25 expression, and FoxP3 expression, as described herein. In further embodiments, the method further comprises administering the expanded regulatory T-cells to a subject in need thereof as described in more detail below.

The iTreg cells obtained using the methods in accordance with this aspect of the invention preferably present all of the following characteristics: expression of the cell surface markers CD4+ and CD25+, expression of FoxP3 (either protein expression as measured by a Western blot and/or FoxP3 mRNA transcription measured, for example, using the methods described or by flow cytometry, Roncador et al., Eur. J. Immunol. 35:1681-1691, 2005); IL-10 independent suppression (measured, for example, in a cytokine assay as described in Example 4); cell-to-cell contact dependent suppression of proliferation of autologous freshly isolated CD4+CD25− responder T-cells which have been stimulated in culture.

FoxP3 expression is also a useful marker for verifying the presence and/or quantitating the number of Treg cells present in the isolated T cell population. Walker et al., J. Clin. Invest. 112:1437-1443, 2003.

Pharmaceutical Compositions

In another aspect, the present invention provides a pharmaceutical composition comprising iTreg cells herein in a formulation which is suitable for administration to a patient in need thereof. In one embodiment, the composition contains a mammalian iTreg cell population. The methods of generating iTreg cells described herein are useful for generating the T-cell population for use in the composition according to this embodiment of the composition of the invention.

In some embodiments, the pharmaceutical compositions according to this aspect of the present invention comprise an iTreg cell population in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans; mannitol; proteins; polypeptides or amino acids such as glycine; antioxidants; chelating agents such as EDTA; adjuvants and preservatives. Compositions of the present invention are preferably formulated for intravenous administration.

In some embodiments, the composition of the present invention contains a therapeutically effective amount of the iTreg cells in combination with an effective amount of another bioactive material.

The pharmaceutical composition comprising iTreg cells herein is administered to a subject in need thereof in a manner appropriate to the disease to be treated and/or prevented. The quantity and frequency of administration will be determined by such factors as the condition of the patient and the type and/or severity of the patient's disease. Appropriate dosages may also be determined by clinical trials. An "effective amount" of the composition can be determined by a physician with consideration of individual differences in age, weight, disease severity, condition of the patient, route of administration and any other factors relevant to treatment of the patient. In general, a pharmaceutical composition comprising iTreg cells may be administered at a dosage of about 105 to 108 cells/kg body weight, preferably 105 to 106 cells/kg body weight, including all integer values within these ranges. The compositions of the invention may also be administered multiple times at these dosages. The optimal dosage and treatment regime for a particular patient can readily be determined by one skilled in the art of medicine by monitoring the patient for signs of disease and adjusting the treatment accordingly.

The cells can be administered by using infusion techniques that are commonly used in immunotherapy, and may be administered to a patient subcutaneously, intradermally, intramuscularly, or by intravenous injection.

Methods of Treating and/or Preventing Autoimmune Diseases and Inflammatory Conditions In another aspect, the present invention provides methods for treating and/or preventing an autoimmune disease or inflammatory condition.

Therefore, immunotherapy with Treg cells obtained from T-cells of a human subject is useful in the context of a cellular therapy for regulating the immune response in the subject. For example, the Treg cells may be used for preventing and/or treating a disease or condition such as an autoimmune disease, inflammatory disease, or in the treatment and/or prevention of transplant rejection and also to prevent graft-versus-host reactions.

Method of Treating and/or Preventing Type 1 Diabetes

The methods of the invention can therefore be used to treat patients with active disease as well as prophylaxis for those identified (based on genetic or antibody screening) as being at risk for developing type 1 diabetes.

Method of Treating and/or Preventing Graft Versus Host Disease

Accordingly, in one aspect, the invention provides a method for reducing the risk of, or the severity of, an adverse GVHD effect in a patient who is undergoing a hematopoietic stem cell transplant, comprising administering to the patient an amount of regulatory T-cells specific for mismatched antigens between the recipient and donor according to the methods described herein effective to reduce the risk or severity of an adverse GVHD effect in the patient.

Method of Treating and/or Preventing an Inflammatory Condition Associated with Organ Transplantation In one embodiment, the invention provides a method of reducing the risk of, or the severity of, an adverse immune response in a patient that has undergone, is undergoing, or will undergo, an organ transplant, comprising administering to the patient an amount of a population of transplant-specific Treg cells according to the methods described herein effective to reduce the risk or severity of an adverse immune response in the patient.

The methods described in this aspect of the invention are useful for reducing the risk of, or the severity of, any adverse immune response in a transplant recipient, such as graft-versus-host disease. The methods may be applied to solid organ (e.g., kidney(s), heart, lung(s), liver and pancreas) transplant recipients or to allogeneic bone marrow or autoimmune patients with autologous or allogeneic bone marrow. A reduction of severity of an adverse immune response may be measured by any suitable method. Non-limiting examples include the reduction or elimination of acute graft rejection, the reduction or elimination of chronic rejection, the reduction or elimination of graft-versus-host disease, and/or the reduction or elimination of the need for high doses of immunosuppressive drugs.

The present cells may also be used in the treatment or prevention of: inflammatory bowel disease, irritable bowel syndrome, multiple sclerosis, Addison's disease, autoimmune hepatitis, autoimmune hypothyroidism, celiac disease, chronic beryllium syndrome, chronic lyme arthritis, familial dilated cardiomyopathy, Goodpasture's syndrome, Graves' disease, insulin autoimmune syndrome, IDDM, juvenile dermatomyositis, Lambert Eaton, myasthenia gravis, pauciarticular juvenile RA, pemphigus foliaceous, PMR, pemphigus vulgaris, rheumatoid arthritis, relapsing polychondritis, scleroderma, sclerosing cholangitis, sjogren's syndrome.

The use of the word "a" or an when used in conjunction with the term "comprising" in the claims and/or the specification may mean "one," but it is also consistent with the meaning of "one or more," "at least one," and "one or more than one."

Also, the use of "comprise", "contain", and "include", or modifications of those root words, for example but not limited to, "comprises", "contained", and "including", are not intended to be limiting. The term "and/or" means that the terms before and after can be taken together or separately. For illustration purposes, but not as a limitation, "X and/or Y" can mean "X" or "Y" or "X and Y".

The term "combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB.

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

In order to facilitate review of the various embodiments of the disclosure, the following explanations of specific terms are provided:

Adjunctive therapy: A treatment used in combination with a primary treatment to improve the effects of the primary treatment.

Clinical outcome: Refers to the health status of a patient following treatment for a disease or disorder or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

Control: A "control" refers to a sample or standard used for comparison with an experimental sample, such as a tumor sample obtained from a patient.

Patient: As used herein, the term "patient" includes human and non-human animals. The preferred patient for treatment is a human. "Patient" and "subject" are used interchangeably herein.

Pharmaceutically acceptable vehicles: The pharmaceutically acceptable carriers (vehicles) useful in this disclosure are conventional. Remington's Pharmaceutical Sciences, by E. W. Martin, Mack Publishing Co. Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Small molecule: A molecule, typically with a molecular weight less than about 1000 Daltons, or in some embodiments, less than about 500 Daltons, wherein the molecule is capable of modulating, to some measurable extent, an activity of a target molecule.

Therapeutic: A generic term that includes both diagnosis and treatment.

Therapeutic agent: A chemical compound, small molecule, or other composition, such as an antisense compound, antibody, protease inhibitor, hormone, chemokine or cytokine, capable of inducing a desired therapeutic or prophylactic effect when properly administered to a subject.

As used herein, a "candidate agent" is a compound selected for screening to determine if it can function as a therapeutic agent. "Incubating" includes a sufficient amount of time for an agent to interact with a cell or tissue. "Contacting" includes incubating an agent in solid or in liquid form with a cell or tissue. "Treating" a cell or tissue with an agent includes contacting or incubating the agent with the cell or tissue.

In certain methods of the invention, there is a further step of administering a cell, tissue, organ, or organism herein (collectively "biological matter") to a patient or in a test model related to modulation of the or in need of the physiological or biological results discussed herein (such as with respect to a particular cellular pathway or result). Consequently, in some methods of the invention there is a step of identifying a patient in need of treatment that can be provided by the cellular modulator(s). It is contemplated that an effective amount of a cellular modulator can be administered in some embodiments. In particular embodiments, there is a therapeutic benefit conferred, where a "therapeutic benefit" refers to an improvement in the one or more conditions or symptoms associated with a disease or condition or an improvement in the prognosis, duration, or status with respect to the disease.

It is contemplated that a therapeutic benefit includes, but is not limited to, a decrease in pain, a decrease in morbidity, a decrease in a symptom. For example, with respect to cancer, it is contemplated that a therapeutic benefit can be inhibition of tumor growth, prevention of metastasis, reduction in number of metastases, inhibition of cancer cell proliferation, inhibition of cancer cell proliferation, induction of cell death in cancer cells, inhibition of angiogenesis near cancer cells, induction of apoptosis of cancer cells, reduction in pain, reduction in risk of recurrence, induction of chemo- or radiosensitivity in cancer cells, prolongation of life, and/or delay of death directly or indirectly related to cancer.

Furthermore, it is contemplated that the compositions may be provided as part of a therapy to a patient, in conjunction with traditional therapies or preventative agents. Moreover, it is contemplated that any method discussed in the context of therapy may be applied as preventatively, particularly in a patient identified to be potentially in need of the therapy or at risk of the condition or disease for which a therapy is needed.

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES

Example 1

Method 1

Figure 2A:
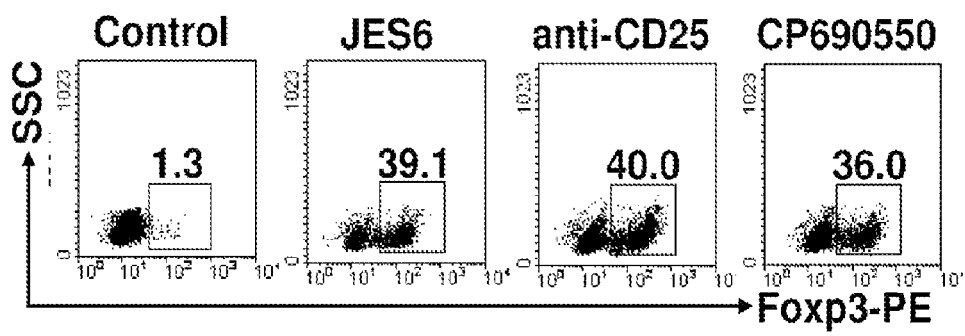
FIGS. 2A-2C. The two-phase induction of regulatory T-cells.
Figure 2B:
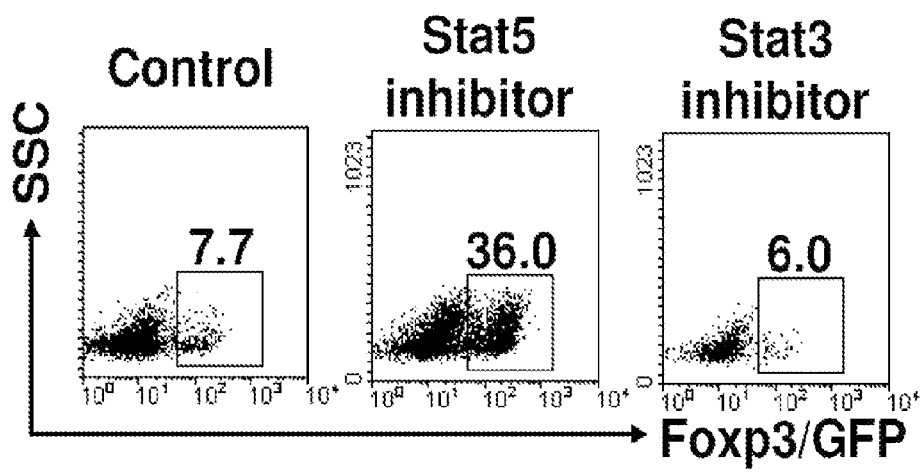

Naïve CD4$^+$ Foxp3/GFP$^-$ cells ($1\times10^6$/ml) cultured in a standard culture medium were stimulated with anti-CD3 monoclonal antibody (mAb)/anti-CD28 MAb in the presence 5 μg/ml anti-IL-2 mAb, or 5 μg/ml anti-CD25 mAb, or 100 nM Janus tyrosine kinase (Jak3) inhibitor (CP-690,550) for 3 days (induction phase). Following washing of cells, medium was replaced with a fresh culture medium supplemented with 10 units/ml recombinant (r)IL-2 and cultured for additional 3 days (expansion phase). In these unique two-phase culture conditions, 36-40% CD4$^+$ Foxp3/GFP$^-$ cells were converted into CD4$^+$CD25$^+$Foxp3/GFP$^+$ iTregs in comparison to 1.3% in controls (FIG. 2A) Similarly, 100 ng/ml Stat5 inhibitor (Stat5 inhibitor) converted 36% of naïve CD4$^+$ Foxp3/GFP$^-$ cells into CD4$^+$CD25$^+$Foxp3/GFP$^+$ iTregs compared to 7% in untreated controls (FIG. 2B).

Figure 2C:
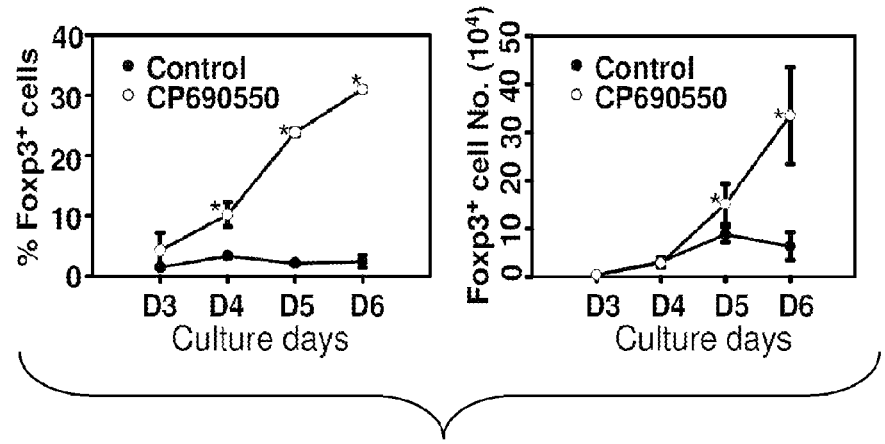

Repeated experiments also showed that an initial 3-day exposure of activated CD4$^+$ Foxp3/GFP$^-$ cells to CP-690,550 induced an 8-fold expansion in the number of iTreg cells, as an initial number of $0.05\times10^6$ CD4$^+$ Foxp3/GFP$^-$ cells resulted on day 6 of culture in an expansion to $0.4\times10^6$ CD4$^+$ CD25$^+$Foxp3/GFP$^+$ cells (FIG. 2C).

Figure 3A:
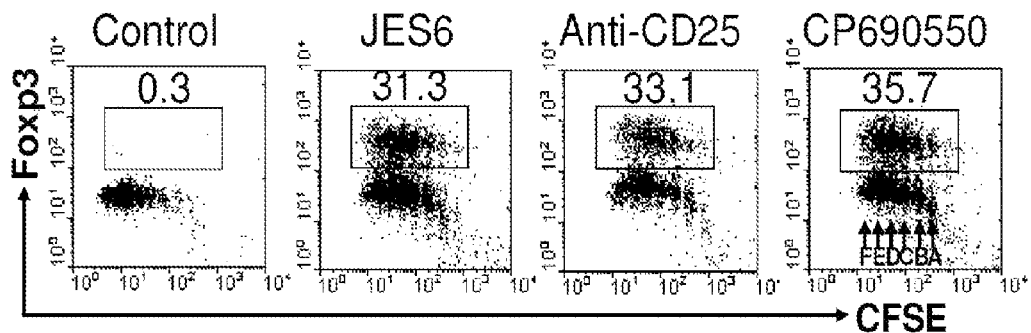
FIGS. 3A-3B. The number of divisions and Foxp3 expression among the two-phase-induced iTreg cells. Naïve mouse CD4$^+$Foxp3/GFP$^-$ cells ($1\times10^6$/ml) were cultured in a medium and stimulated with anti-CD3 mAb/anti-CD28 mAb in the presence of 5 µg/ml anti-IL-2 mAb, 5 µg/ml anti-CD25 mAb, or 100 nM Janus tyrosine kinase (Jak3) inhibitor (CP-690,550) for 3 days. After washing, fresh medium with 10 units/ml rIL-2 was added to culture for additional 3 days. FACscan analysis of CD4$^+$Foxp3/GFP$^+$ cells was performed for each cultured population without (first panel) or with different inhibitory factors (last 3 panels) (FIG. 3A). Following stimulation in the presence of CP-690,550, each divided cell population was examined for the Foxp3 expression (FIG. 3B).
Figure 3B:
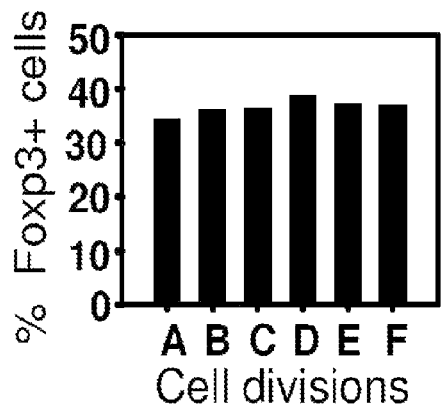
Figure 4A:
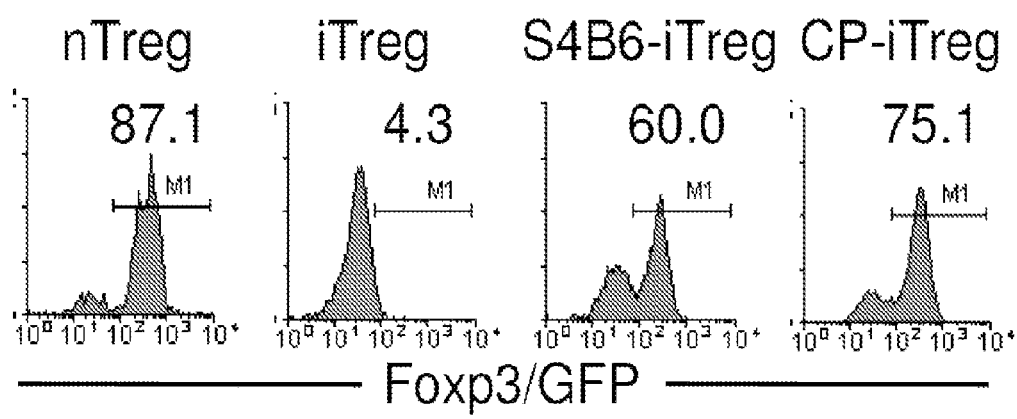
FIGS. 4A-4B. Stability of Foxp3 expression and suppressor function of the two-phase induced iTreg T cells. The nTreg cells were isolated from spleen of naïve mice (left panel). Naïve mouse CD4$^+$Foxp3/GFP$^-$ cells ($1\times10^6$/ml) cultured with APCs were stimulated with anti-CD3 mAb in the presence of 5 ng/ml TGF-β, 5 µg/ml anti-IL-2 mAb (S4B6), or 100 nM CP-690,550 for 3 days. After washing, fresh medium was supplemented with 10 units/ml rIL-2 and cultured for additional 3 days (total 6 day culture). All these 4 populations were subsequently re-stimulated with anti-CD3 mAb/anti-CD28 mAb for 3 days and examined by FACscan for Foxp3 expression (FIG. 4A). Purified naive CD4$^+$Foxp3/GFP$^-$ cells labeled with CFSE were used as T-effector (Teff) cells and mixed with re-stimulated nTreg cells or re-stimulated CP-690,550-induced iTreg cells. Proliferation was measured by the number of Teff cell divisions (FIG. 4B).

When cell divisions were examined in a 6-day culture, the CP-690,550-induced iTreg cells maintained similar levels of Foxp3 expression during proliferation (FIG. 3A and FIG. 3B). Furthermore, the stability of Foxp3 expression of anti-IL-2 mAb-(S4B6) or Jak3 inhibitor (CP-690,550)-induced iTregs was compared with TGF-β-induced iTregs. Following repeated re-stimulation with anti-CD3/anti-CD28 mAbs, 80% of nTreg cells (isolated as CD4$^+$ Foxp3/GFP$^+$), 60% of anti-IL-2 mAb-induced iTreg cells, and 75% of CP-690,550- induced iTreg cells maintained Foxp3 expression in comparison to only 4.3% of re-stimulated TGF-β-induced iTreg cells (FIG. 4A).

Figure 4B:
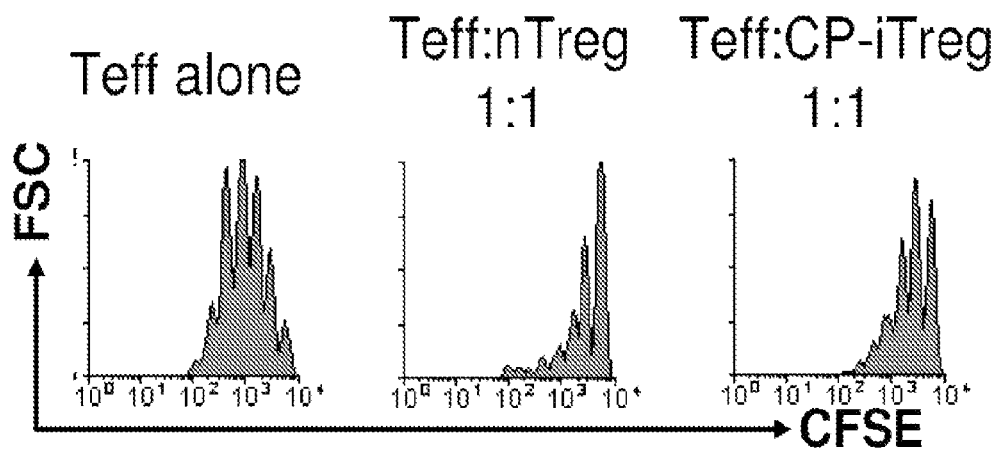

In addition, a co-mixing experiment of T effector (Teff) to nTreg or iTreg cells (at 1:1 ratio) showed that both nTreg and CP-690,550-induced iTreg cells maintained very potent suppressor function even after repeated re-stimulation (FIG. 4B). These results document that a two-phase culture method produces stable and potent iTreg cells.

Example 2

Method 2

Figure 5:
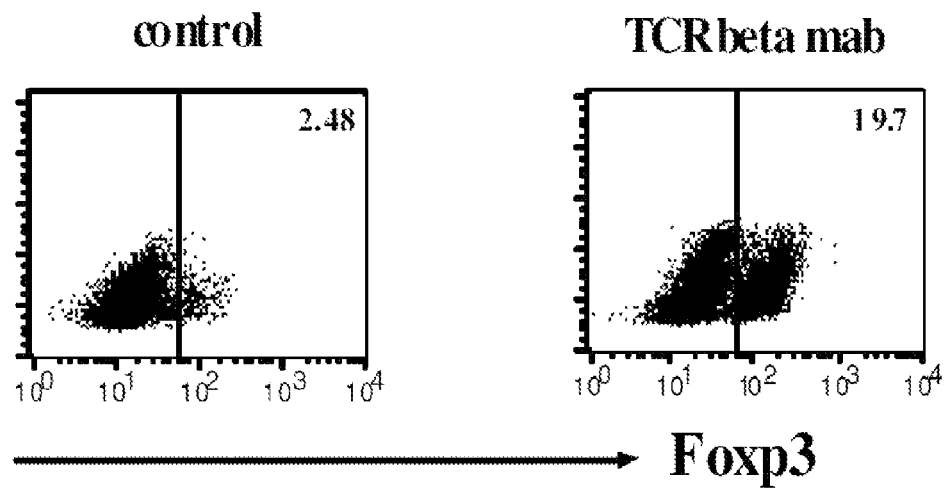
FIG. 5. Induction of Treg cells by stimulation with TCRβ mAb. Naïve spleen cells ($1\times10^6$/ml) were cultured in medium and stimulated with 5 µg/ml TCRβ mAb for 3 days; after washing cells were cultured for additional 3 days with rIL-2. FACS analysis was performed to show expression of CD4$^+$ Foxp3/GFP$^+$ Treg cells.

Naïve CD4$^+$ Foxp3/GFP$^-$ cells (1×10$^6$/ml) cultured in standard culture medium are stimulated with anti-CD3 mAb/anti-CD28 mAb in the presence of 5 μg/ml anti-TCRβ mAb for 3-4 days. Following stimulation, medium was replaced with the fresh culture medium supplemented with 10 units/ml rIL-2 and cultured for next 3-4 days. The two-phase culture conditions with anti-TCRβ mAb converted CD4$^+$ Foxp3/GFP$^-$ cells into 19.7% of Foxp3/GFP$^+$ cells compared to only 2.5% in controls (FIG. 5). The stability (Foxp3 expression) of TCRβ-induced iTregs was compared with TGF-β-induced iTregs (not shown). The results confirmed that repeated re-stimulation of TCRβ-expanded iTregs maintained expression of Foxp3 and suppressor function.

Example 3

Method 3

Figure 6:
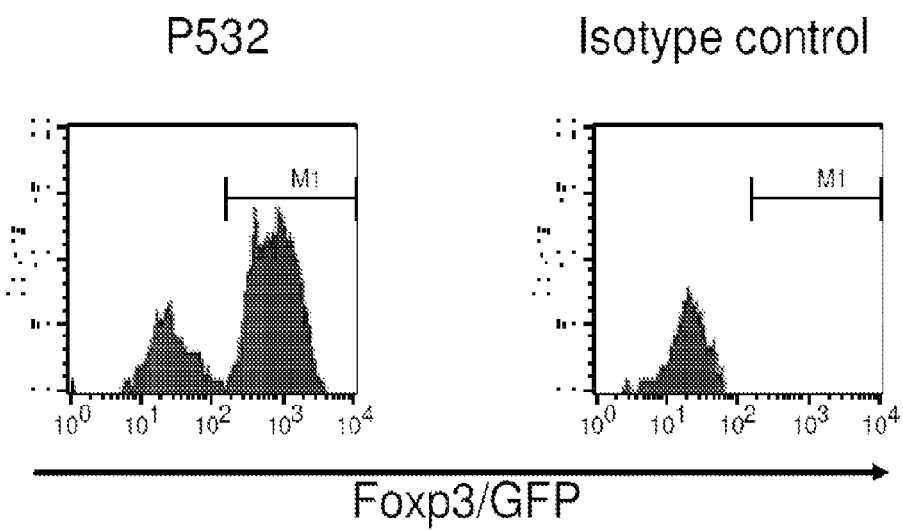
FIG. 6. Induction of Treg cells in cultures with anti-CD11a mAb. Naïve CD4$^+$Foxp3/GFP$^-$ cells ($1\times10^6$/ml) were cultured in medium with APCs and stimulated with anti-CD3 mAb in the presence of 5 µg/ml anti-CD11a mAb for 3 days. After washing, cells were cultured in medium with 10 units/ml rIL-2 for additional 3 days and FACS analysis was performed to show expression of Foxp3/GFP (left panel). Cultures of spleen cells used as APCs were also labeled with isotype Ab (right panel).

Naïve CD4$^+$ Foxp3/GFP$^-$ cells (1×10$^6$/ml) cultured in standard culture medium with syngeneic APCs were stimulated with anti-CD3 mAb in the presence of 5 μg/ml anti-CD11a mAb (P532) for 3 days. Following washings, medium was replaced with a fresh medium with 10 units/ml rIL-2 and cultured for next 3 days. The unique two-phase culture conditions converted 73.3% of CD4$^+$ Foxp3$^-$ cells into CD4$^+$CD25$^+$Foxp3$^+$ iTregs (FIG. 6; left panel) whereas controls were ineffective (FIG. 6; right panel).

The stability (Foxp3 expression) of anti-CD11a-mAb-induced iTregs was confirmed in comparison with TGF-β-induced iTregs (not shown). In particular, re-stimulated anti-CD11a mAb-induced iTregs maintained Foxp3 expression in contrast to TGF-β-induced iTreg cells. These results confirmed that stimulation with anti-CD11a mAb in the inventors' unique culture conditions promoted generation of stable iTreg cells.

Example 4

In Vivo-Related Materials and Methods

Mice

BALB/c, C57BL/6 (B6), C31-1, NOD/ShiLtJ (NOD), C57BL/6-Tg(BCL2)25Wehi/J (Bcl-2 Tg), B6.Cg-FoxP3tm2Tch/J (FoxP3/GFP), B6-Tg(Ins2-OVA)59Wehi/WehiJ (RIP-OVA$^{hi}$), and B6.Cg-FoxP3$^{sf}$/J (FoxP3$^{sf}$) mice were purchased from the Jackson laboratory (Bar Harbor, Me.). B6.SJL, B6.129S7-Rag1$^{tm1Mom}$Tg(TcraTcrb)1100Mjb (OT-I/Rag1$^{-/-}$), and B6.129S7-Rag1$^{tm1Mom}$Tg(TcraTcrb)425Cbn (OT-II/Rag1$^{-/-}$) mice were obtained from Taconic Farms, Inc. (Hudson, N.Y.). Animals were maintained at the University of Toledo specific pathogen-free animal facility according to institutional guidelines.

Reagents

Fluorescence conjugated anti-mouse CD4, CD8, CD45.2, Vβ8, and Vβ2 mAbs were purchased from BD Biosciences (San Jose, Calif.) or eBioscience (San Diego, Calif.). Purified anti-CD3 (clone 145-2C11) and anti-TCR (clone H57-597) mAbs were obtained from eBioscience or Bio X Cell (West Lebanon, N.H.). Anti-FoxP3-PE and intracellular staining kit were purchased from eBioscience. CFDA SE (CFSE) Cell Tracer Kit was obtained from Invitrogen (Carlsbad, Calif.). Murine rIL-2 was purchased from Peprotech (Rocky Hill, N.J.). Mouse IL-2, IL-6, IFN-γ, and TNF-α DuoSet ELISA kits were purchased from R&D Systems (Minneapolis, Minn.). Staphylococcal enterotoxin B (SEB) was obtained from Sigma-Aldrich (St. Louis, Mo.). OVA (257-264) and OVA (323-339) peptides were obtained from GenScript (Piscataway, N.J.).

Cell Preparation and Cultures

Single cell suspensions from spleens of 8-10 week old B6, FoxP3/GFP, B6-SJL or OT-1 mice (2.0×10$^5$ cells/well) were cultured in 96-well round-bottom plates with or without appropriate stimulations as described in the text. For measuring cell proliferation, cell cultures were labeled with 1 μCi/well [H$^3$] thymidine during the final 18 hrs and incorporated radioactivity was determined by a microplate scintillation counter (Packard, Ramsey, Minn.). For monitoring FoxP3 expression, some cultures were harvested at day-3, washed and transferred to 10 IU/ml IL-2 containing RPMI media and rested for 3 days. FoxP3 expression was analyzed in the 3 day- or 6 day-cultures by measuring GFP fluorescence or by intracellular anti-FoxP3-PE staining. To distinguish between Treg conversion versus expansion, similar cultures were performed using sorted FoxP3/GFP$^-$ splenocytes from FoxP3/GFP mice.

In Vitro Suppression Assay

A total of 5×10$^4$/well CD4$^+$CD25$^-$ T-cells sorted from B6 mice and labeled with 1 μM CFSE prior to cultures were used as responder cells. Suppressors were FoxP3/GFP$^+$ cells sorted out from day-6 cultures. FoxP3/GFP$^+$ naturally occurring Treg (nTreg) cells were sorted ex vivo from FoxP3/GFP mice. Treg cells were seeded in 1:1 ratio of suppressor:responder cells. Cells were cultured in the presence of 1.5×10$^5$/well syngeneic APCs (Sorted CD3$^-$ splenocytes) and soluble anti-CD3 mAb (0.5 μg/ml) for 3 days. Proliferation of responder cells was measured by CFSE dilution on day 3 cultures by flow cytometric analysis.

In Vivo Response to SEB 6-8 wks old B6 mice were injected i.v. with 150 μg SEB (Sigma, St Louis) alone or co-injected i.p. once with 1 mg/kg of H57-597 mAb. Single cell suspensions from spleens and lymph nodes of controls and treated groups were examined at days 0, 3, 6 and 10, and analyzed for frequencies of Vβ8$^+$ and Vβ2$^+$ cells within CD4 and CD8 T-cell populations by flow cytometric analysis.

Cytokine Measurements by ELISA and Bio-Plex

Mice were injected i.p. with 1 mg/kg 145-2C11 mAb, H57-597 mAb or isotype control antibodies. At 1.5, 4, 12 and 24 hrs after injection sera were analyzed for IL-2, IL-6, IFN-γ, and TNF-α levels by quantitative mouse Duoset ELISA kits from R&D Systems as well as Bio-Plex Pro Cytokine reagent kit from Bio-Rad. ELISA plates were read using a VERSAmax tunable microplate reader from Molecular Devices (Sunnyvale, Calif.), and Bio-Plex plates were analyzed using a Bio-Plex 200 (Bio-Rad, Hercules, Calif.).

Type 1 Diabetes Induction in RIP-OVA$^{hi}$ Mice

RIP-OVA$^{hi}$ mice expressing OVA in the pancreatic β cells were adoptively transferred with 5×10$^5$ purified OVA-specific CD8$^+$ T-cells from Rag2/OT-I mice, 1×10$^6$ OVA-specific CD4$^+$ T-cells from Rag2/OT-II mice, and 2×10$^5$ BM-derived dendritic cells pulsed with 10 μg/ml OVA$_{323-339}$ peptide. RIP-OVA$^{hi}$ mice were then injected i.p. with either PBS or a single dose of 1 mg/kg H57-597 mAb. Mice were then monitored for blood glucose concentrations for respective time points as stated in the text using ReliOn Ultima glucose meter (Abbott Diabetes Care Inc, Alameda, Calif.).

Type 1 Diabetes in NOD Mice

Prevention of TID: 8-week old NOD mice were injected i.p. with 4 doses (once a week for 4 weeks) of 1 mg/kg 145-2C11 mAb, 1-157-597 mAb, or isotype control antibodies and monitored for blood glucose levels until 26 weeks. Mice that maintained blood glucose levels of ≤250 mg/dL were considered to be diabetes free.

Remission of TID:

Spontaneous new-onset diabetic NOD mice (two consecutive blood glucose concentrations between 250 and 350 mg/dL) were treated daily for 10 days with PBS or 1 mg/kg of H57-597 mAb i.p. and subsequently monitored for blood glucose levels.

Heart Transplantation and Histology

Heart transplantation was performed by a previously described method (20). In brief, hearts from either C3H (H-2$^k$) or Balb/c donors were transplanted to B6 or Rag1−/− recipients. Heart graft survival was monitored daily by palpation, and the day of complete cessation of heartbeat was considered as the day of rejection. Allografts were sectioned and stained with Hematoxylin/Eosin for microscopic evaluation.

Statistical Analysis

The results of the graft survival data were analyzed by Mann Whitney test. All other statistics were evaluated using the unpaired Student's t-test method to document statistical significance. The p values of <0.05 were considered as statistically significant.

Example 5

Figure 1:
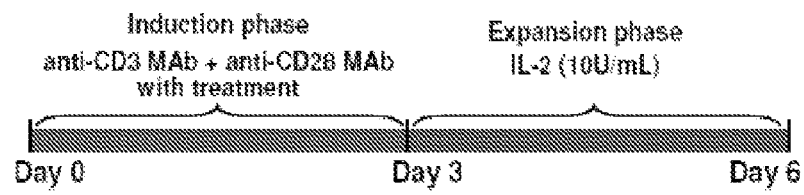
FIG. 1. A two-phase induction and expansion protocol to produce large numbers of iTreg cells.
Figure 7A:
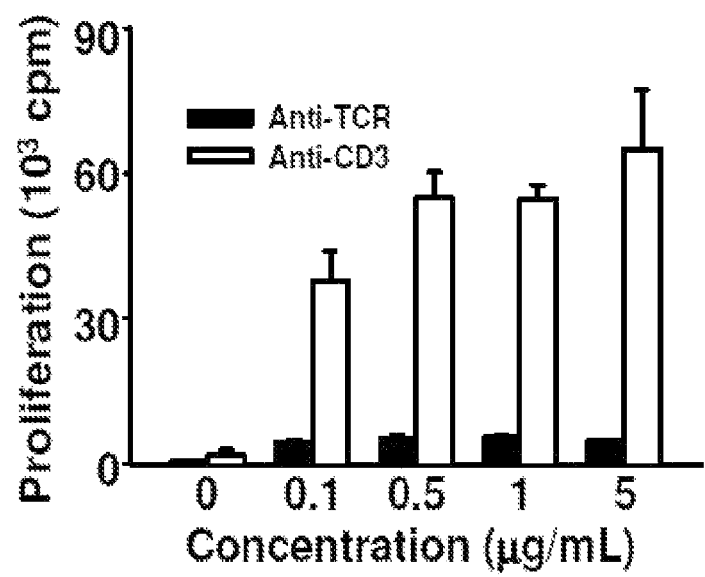
FIG. 7A-7E. Anti-TCR mAb, H57-597, inefficiently stimulates T-cell proliferation but enriches FoxP3$^+$ Treg cells in vitro. (7A) $2\times10^5$ splenocytes were cultured in each well of the 96-well-plate and supplemented with either soluble H57-597 mAb or an anti-CD3 mAb (145-2C11) at the indicated concentrations. Cell proliferation was assessed on day 3 by $^3$H-thymidine incorporation. (7B) The cartoon illustrates the culture system used in C and E to assess H57-597 mAb treatment effects on in vitro T-cell responses. (7C) Whole splenocytes (top 3 panels) or FoxP3/GFP$^-$ splenocytes (bottom panel) isolated from FoxP3/GFP mice were stimulated for 3 days with 0.1 µg/ml of 145-2C11 mAb alone (none group), or further supplemented with 5 µg/ml H57-597 mAb (Anti-TCRβ group) or isotype Ab (Isotype group). On day 3, cultured cells were washed and then rested with 10 IU/ml IL-2 only for an additional 3 days. The dot plots show the frequencies of FoxP3/GFP$^+$ cells gated on the CD4$^+$ cell population in the day-3 or day-6 cultures. (7D) $5\times10^4$ CFSE-labeled CD4$^+$CD25$^-$ T-cells were stimulated with syngeneic APCs and soluble anti-CD3 mAb (Teff alone), or further co-cultured with $5\times10^4$ CD4$^+$FoxP3/GFP$^+$nTreg cells (nTreg:Teff) or CD4$^4$FoxP3/GFP$^4$ cells sorted out from the day-6 cultures of the above anti-TCRβ group (anti-TCR-Treg:Teff). Histograms show CFSE fluorescence staining within the CFSE$^+$cell population at culture day 3. (7E) Whole splenocytes from CD45.2$^-$ SJL mice were co-cultured with FoxP3/GFP splenocytes from CD45.2$^+$ FoxP3/GFP mice at 1:1 ratio in the presence of both 145-2C11 mAb and H57-597 mAb for 3 days, followed by resting in IL-2 containing medium for 3 days. Histograms shows the frequencies of FoxP3-expressing cells gated on CD45.2$^-$CD4$^+$ (left panel) or CD45.2$^+$CD4$^+$ (right panel) in the day-6 cultures.
Figure 7B:
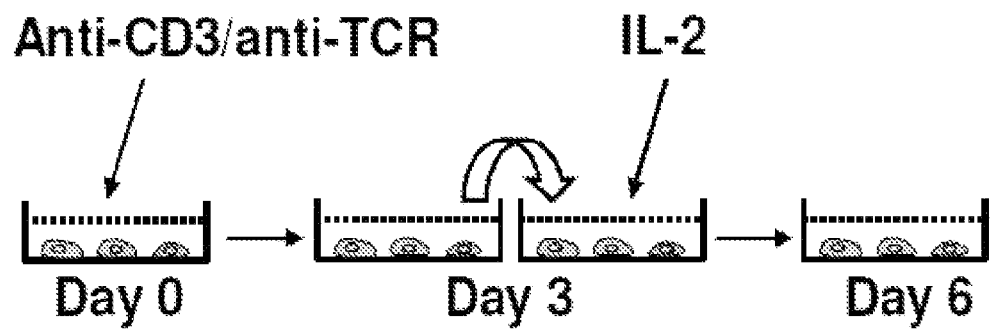
Figure 7C:
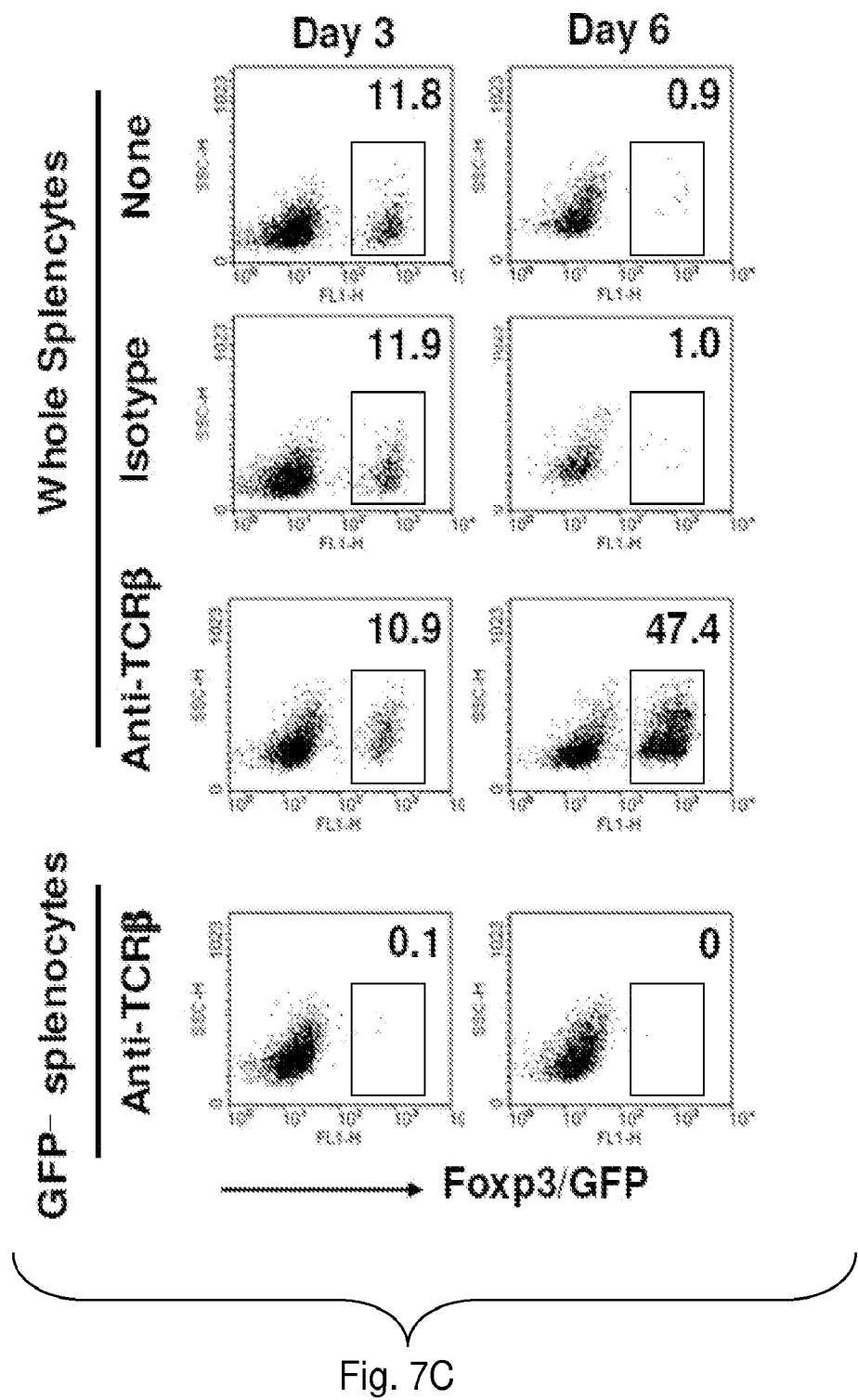
Figure 7D:
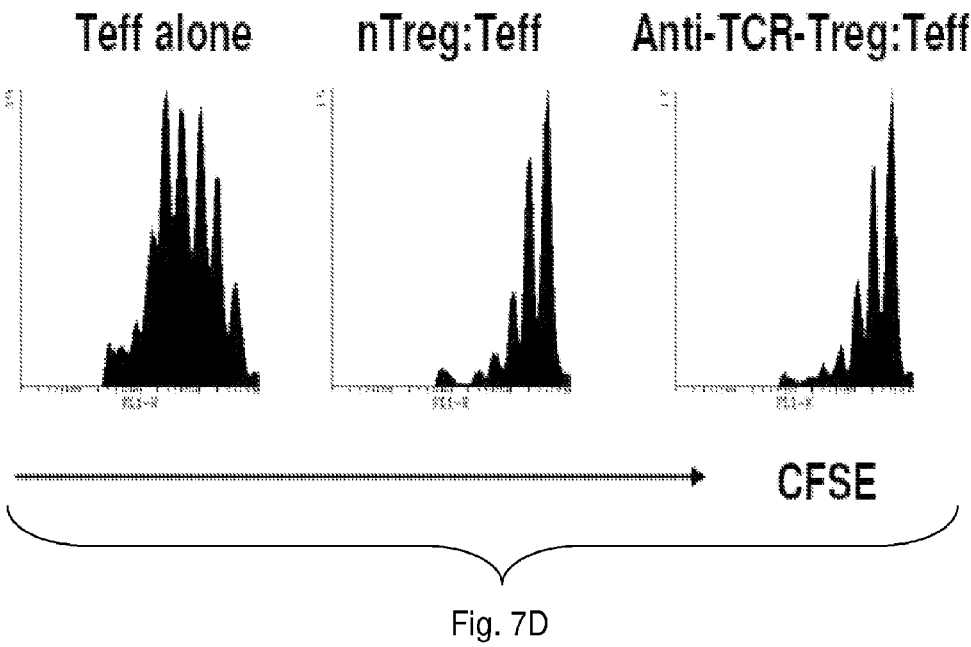
Figure 7E:
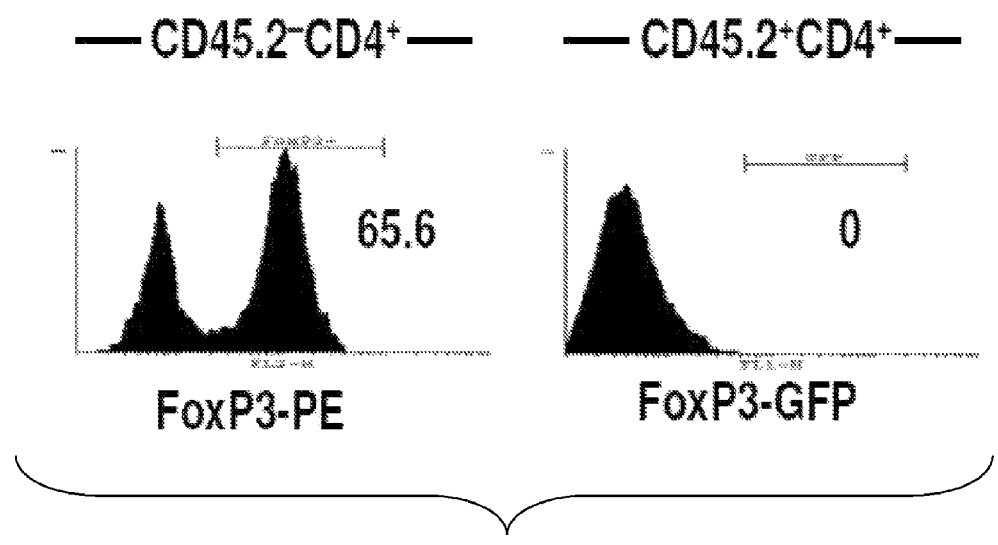
Figure 13:
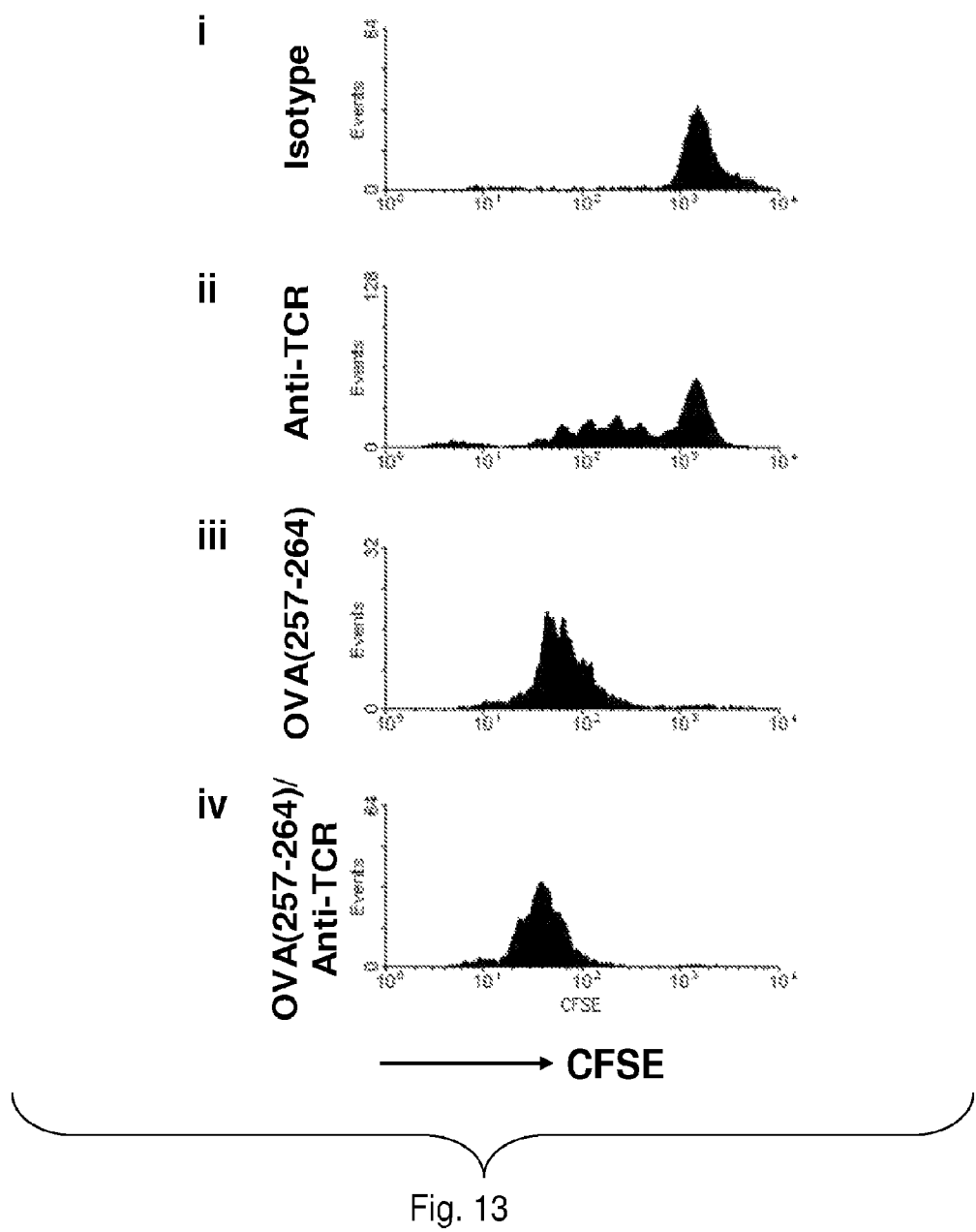
FIG. 13. H57-597 mAb induces limited proliferation compared to specific antigen stimulation in vitro.

TCR-Specific H57-597 mAb Exhibited Very Limited Mitogenic Effects on T-Cells but Enriched FoxP3-Expressing Treg Cells In Vitro To determine its immune regulatory effects, the anti-mouse TCRβ mAb (clone H57-597) was tested in cultures. As shown in FIG. 7A, even the higher concentrations of H57-597 mAb were ineffective when compared with the T-cell proliferation induced by anti-mouse CD3 mAb (clone 145-2C11). Addition of 5 μg/ml H57-597 mAb into the culture of CFSE-labeled OT-I splenocytes induced limited T-cell proliferation when compared to that induced by 5 μg/ml OVA$_{257-264}$ (FIG. 13). To further determine the effects of H57-597 mAb, splenocytes from FoxP3/GFP reporter mice were stimulated for 3 days with 0.1 μg/ml soluble anti-CD3 mAb alone (None group) or together with 5 μg/ml H57-597 mAb (Anti-TCRβ group) or isotype Ab control (Isotype group). The cultures were washed and rested with 10 IU/ml IL-2 alone for an additional 3 days (FIG. 7B). While no significant difference was observed on day 3, FoxP3/GFP$^+$ cells were enriched (47.4% within CD4$^+$ cells) on day 6 only in cultures treated with H57-597 mAb (FIG. 7C; Anti-TCRβ group). These Treg cells potently inhibited the proliferation of CFSE-labeled effector T-cells (FIG. 7D; right panel), similar to nTreg cells (FIG. 1D; middle panel). In contrast, few FoxP3/GFP$^+$ Treg cells (~1% within CD4$^+$ cells) were present in the day-6 cultures of anti-CD3 mAb alone or with isotype Ab (FIG. 7C; None or Isotype group). To examine whether Treg cells in the anti-TCRβ mAb-treated group were expanded nTreg cells or converted from FoxP3$^-$ naïve T-cells, identical in vitro cultures (FIG. 7B) were prepared with sorted FoxP3/GFP$^-$ splenocytes (FIG. 7C; lower panel) or with a 1:1 mixture of sorted CD45.2$^+$ FoxP3/GFP$^-$ and CD45.1$^+$ splenocytes (FIG. 7E). Addition of H57-597 mAb to anti-CD3 mAb stimulated FoxP3/GFP$^-$ splenocytes did not convert them into FoxP3-expressing cells (FIG. 7C). In addition, none of the CD45.2$^+$ FoxP3/GFP$^-$ cells were converted into FoxP3-expressing cells even in the presence of CD45.2$^-$ splenocytes containing nTreg cells (FIG. 7E; right panel). In contrast, FoxP3-expressing cells were enriched within the CD45.2$^-$ population (FIG. 7E; left panel). Therefore, anti-TCRβ mAb enriches (but does not generate) suppressive FoxP3-expressing CD4 cells during CD3-mediated T-cell responses while exerting limited mitogenic effects on naïve T-cells in vitro.

Example 6

Figure 8A:
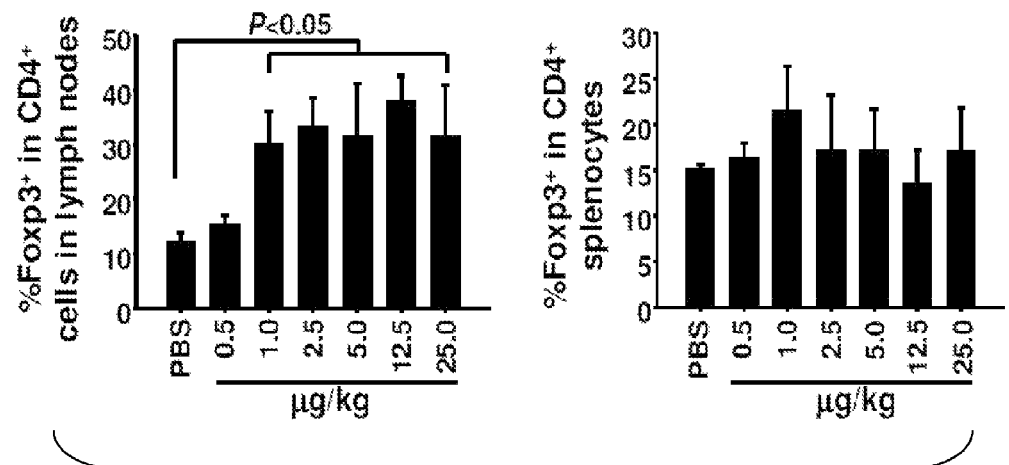
FIG. 8A-8D. H57-597 mAb-treatment reduces T-cell numbers, enriches Treg cells, and arrests T-cell response to the SEB superantigen in vivo. (8A-8B) B6 mice were injected once with PBS or H57-597 mAb at the indicated doses. Five days later, cells were isolated from the secondary lymphoid organs for ex vivo analysis. In A, bar graphs show the frequencies of FoxP3$^+$cells among CD4 cell population in lymph nodes (left panel) and spleens (right panel). In B, bar graphs show the number of CD4 (left panel) or CD8 (right panel) cells in spleens. (8C) Bcl-2 Tg or wild type B6 mice received a single injection of 1 mg/kg H57-597 mAb. Histograms show the frequencies of FoxP3$^+$ cells among CD4 cell population in spleens of Bcl-2 Tg (left panel) and wild type (right panel) mice at day 5 after injection. (8D) B6 mice were injected with either 150 µg SEB alone (solid lines) or together with 1 mg/kg H57-597 mAb (dashed lines). Splenocytes were isolated at the indicated days after injection, and the frequencies of Vβ8 and Vβ2 among CD4 (left panel) or CD8 (right panel) cell populations are shown.
Figure 8B:
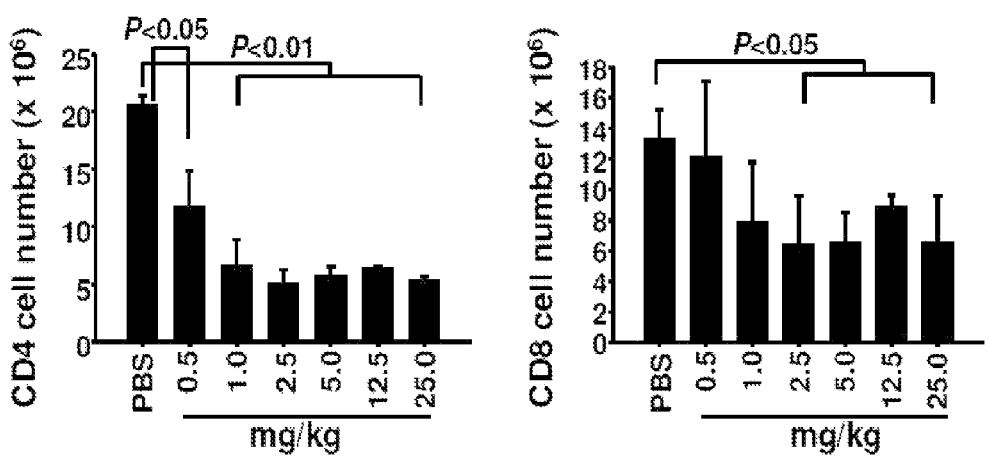
Figure 8C:
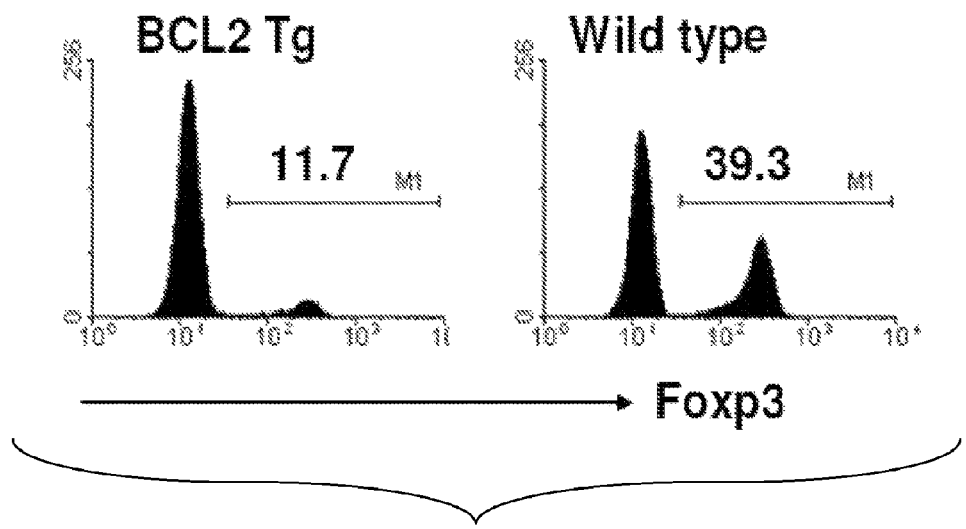

H57-597 mAb Enriched FoxP3-Expressing Treg Cells and Diminished Antigen-Reactive T-Cells In Vivo To investigate the in vivo immune regulatory effects of TCR-specific mAb, the inventors assessed wild-type mice 5 days after injection once with H57-597 mAb. Consistent with the in vitro observations, 1 mg/kg or higher doses of H57-597 mAb elevated the frequency of CD4$^+$FoxP3$^+$ Treg cells among CD4$^+$cells in lymph nodes by ~3-fold to 30-40% (FIG. 8A; left panel) and in spleens by 2-fold to 20% (FIG. 8A; right panel). Because H57-597 mAb reduced CD4$^+$ by ~60% and CD8$^+$ by ~40% (FIG. 8B), it is possible that the Treg enrichment resulted from the anti-TCR mAb-induced death of conventional T-cells but not Treg cells. To test this possibility, the inventors used Bcl-2 Tg mice in which conventional T-cells are resistant to apoptosis (22). In contrast to the wild-type mice, H57-597 mAb failed to reduce T-cell numbers (data not shown) and consequently the frequency of Treg cells in Bcl-2 Tg mice (FIG. 8C). Thus, Treg cells in wild-type mice were relatively resistant to H57-597 mAb-induced death compared to conventional T-cells. A gradual recovery of the T-cell homeostasis in H57-597 mAb-treated wild-type mice was observed within 40-100 days (FIG. 14).

Figure 8D:
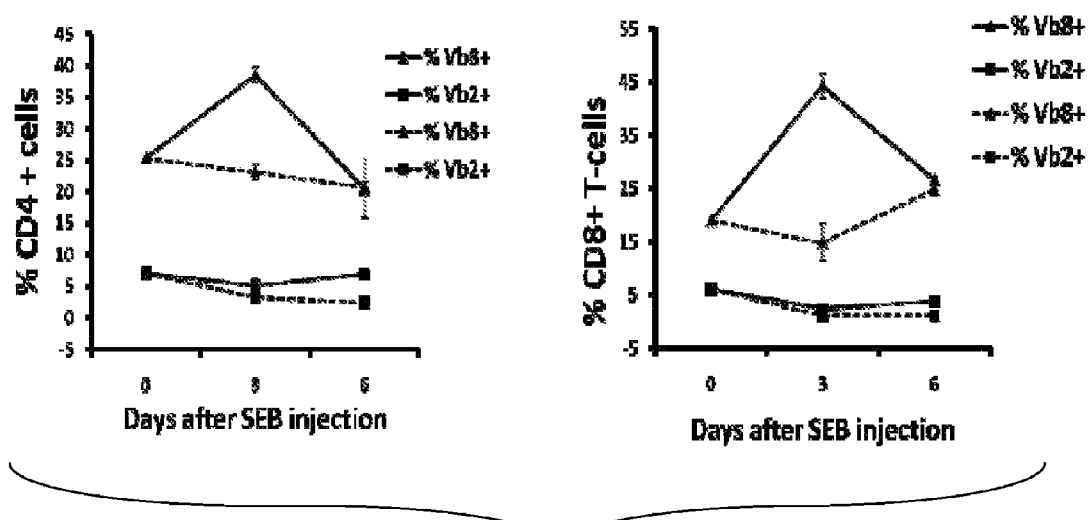

The inventors next determined the effects of TCR-specific mAb during an ongoing antigen response of T-cells. Wild-type B6 mice injected with 150 μg superantigen staphylococcal enterotoxin B (SEB) were treated once with 1 mg/kg H57-597 mAb or PBS. The frequencies of SEB-reactive Vβ8$^+$ and SEB-nonreactive Vβ2$^+$ T-cells in the lymphoid organs were tracked on days 0, 3, 6 and 10 after SEB injection. In the PBS-treated group, the percent of Vβ8$^+$ (but not Vβ2$^+$) CD4$^+$ and CD8$^+$ T-cells dramatically expanded on day 3 and contracted on day 6. In contrast, H57-597 mAb abrogated the expansion of Vβ8+ T-cells with little effect on Vβ2$^+$ T-cells (FIG. 8D). Therefore, H57-597 mAb not only reduces the total T-cell numbers and enriches Treg frequencies, but also selectively arrests the expansion of antigen-reactive T-cells.

Example 7

Limited Cytokine Production Upon TCR Engagement with H57-597 mAb In Vivo

Figure 9A:
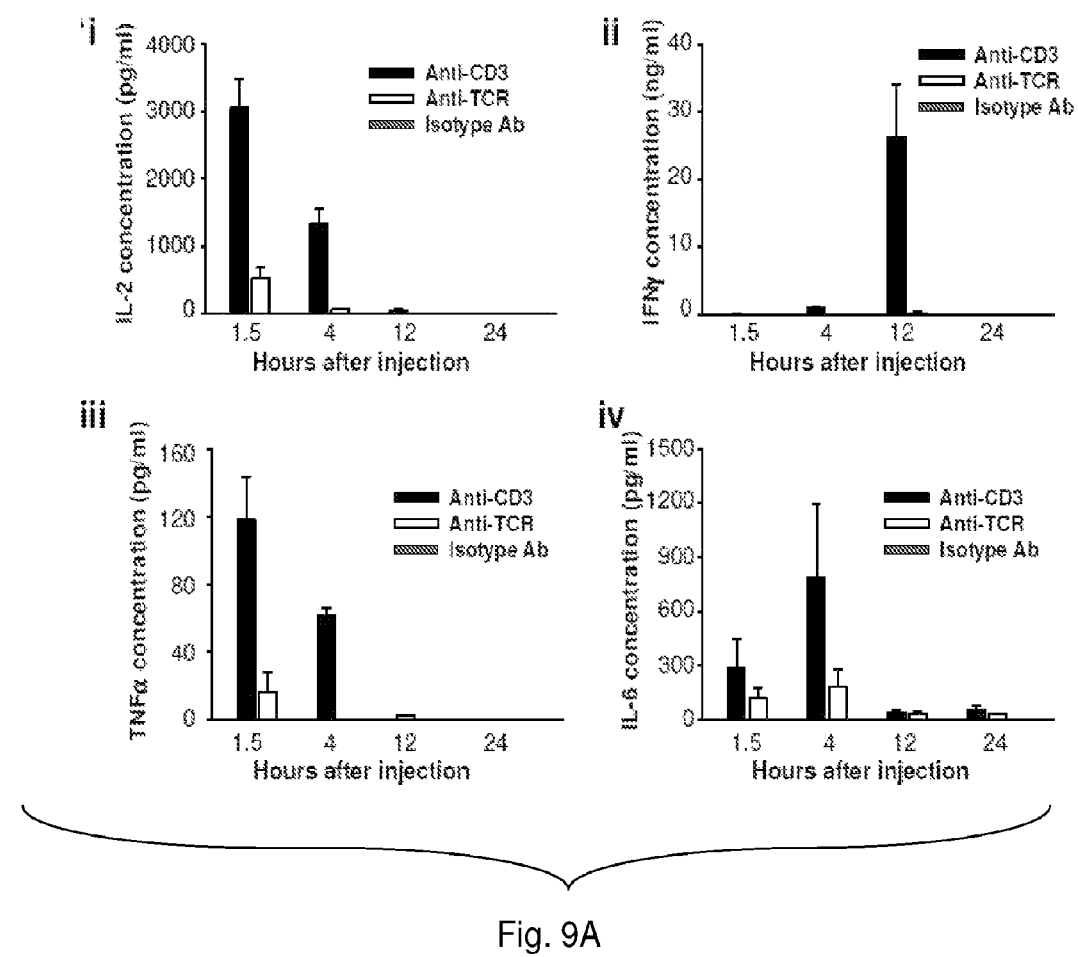
FIG. 9A-9B. Cytokine production in vivo after H57-597 mAb treatment. (9A) B6 mice were injected with 1 mg/kg anti-CD3 mAb (145-2C11), anti-TCR mAb (H57-597), or isotype Ab for H57-597 mAb. Mice were euthanized at the indicated hours after injection, and the serum levels of IL-2 (i), IFN-γ (ii), TNF-α (iii), and IL-6 (iv) were assessed by ELISA assay and shown in bar graphs. (9B) B6 mice were injected with PBS, anti-CD3 mAb, or anti-TCR mAb at the indicated concentrations. Mice were euthanized at 4 hours after injection to assess the serum levels of IL-2 (i), TNF-α (iii), and IL-6 (iv) by ELISA assay, or at 12 hours after injection to assess the serum level of IFN-γ (ii). Each time point represents measurements from 3 mice (* indicates p<0.05 between the anti-CD3 mAb and anti-TCR mAb treated groups).
Figure 9B:
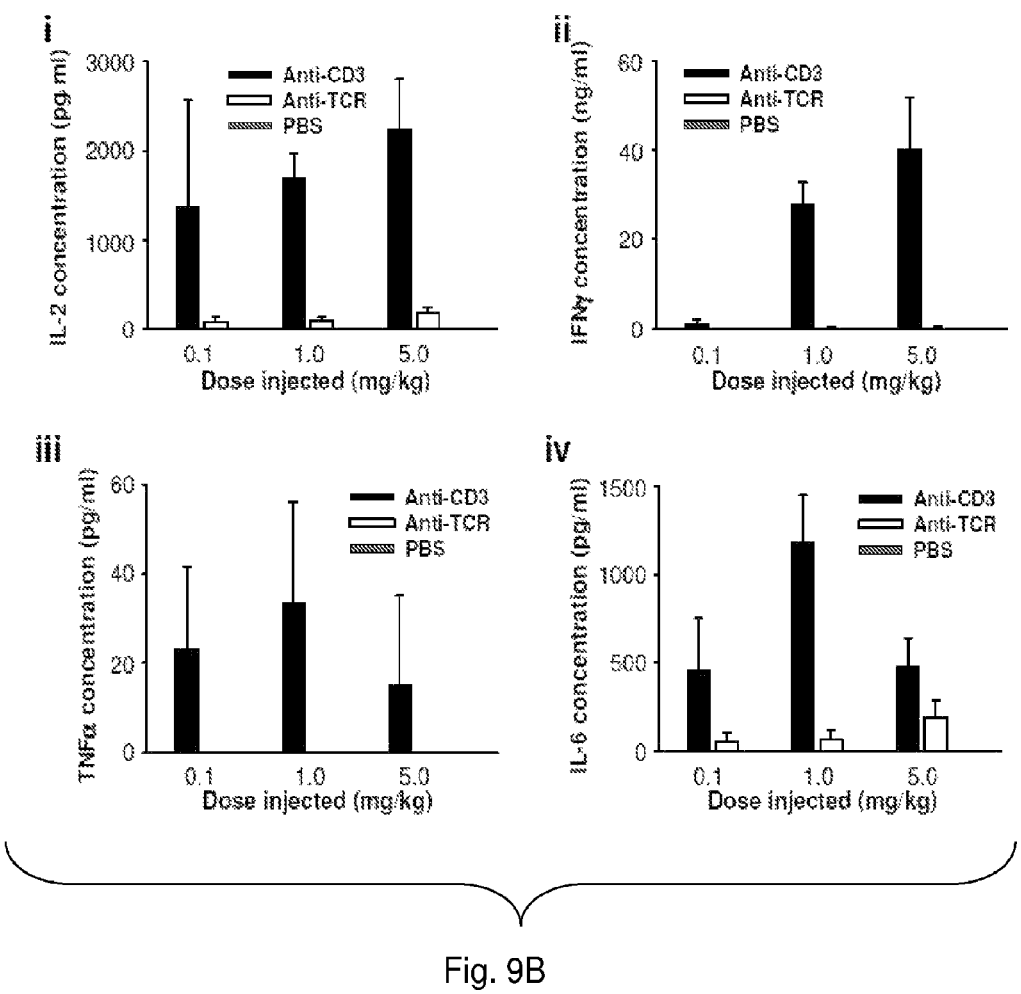

Agonist antibodies binding to the TCR-CD3 complex in vivo may trigger undesired cytokine storm. The inventors thus compared the effects of H57-597 mAb and anti-CD3 mAb (clone 145-2C11) on in vivo cytokine production. As shown in FIG. 9A, serum levels of IL-2, IL-6, IFN-γ, and TNF-α were undetectable at all tested time points in isotype Ab control group. Conversely, 1 mg/kg 145-2C11 mAb injection significantly elevated the serum levels of IL-2, IL-6, and TNF-α at both 1.5 and 4 hrs, and IFN-γ at 12 hrs. Importantly, 1 mg/kg H57-597 mAb produced only low levels of the same cytokines at all tested time points (FIG. 9A). Bio-Plex analysis confirmed the measured serum cytokine levels (FIG. 15). Moreover, in contrast to sera of mice injected with 145-2C11 mAb, various doses of 0.1, 1, or 5 mg/kg H57-597 mAb elicited significantly lower levels of serum IL-2 and IL-6, and undetectable IFN-γ and TNF-α (FIG. 9B). In conclusion, the in vivo cytokine release after TCR engagement with anti-TCR mAb is minimal when compared to that observed with anti-CD3 mAb.

Example 8

H57-597 mAb Prevented T1D as Well as Reversed the Onset of T1D

Figure 10A:
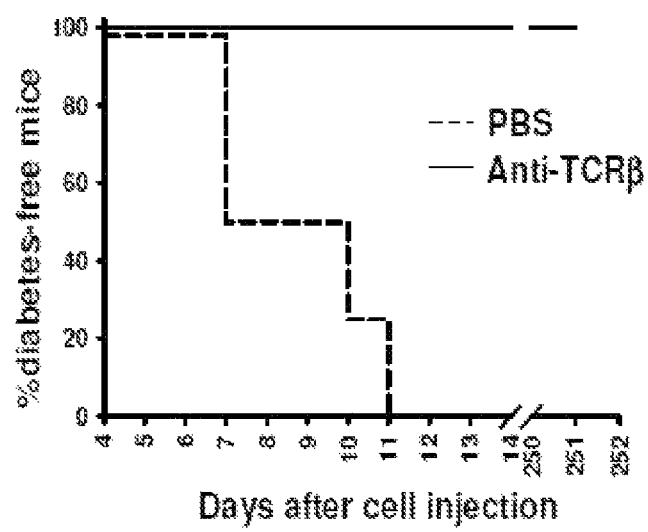
FIG. 10A-10B. A single injection of H57-597 mAb abrogates the onset of T1D in RIP-OVA$^{hi}$ mice induced by transferred OVA-specific T-cells. RIP-OVA$^{hi}$ mice were adoptively transferred with 5×10$^5$ CD8$^+$ T-cells from Rag2/OT-1 mice, 1×10$^6$ CD4$^+$ T-cells from Rag2/OT-II mice, and 2×10$^5$ BM-derived dendritic cells pulsed with 10 μg/ml OVA$_{323-339}$ peptide. RIP-OVA$^{hi}$ mice were then injected with either PBS or a single dose of 1 mg/kg H57-597 mAb. Blood glucose concentrations were monitored. (10A) The graph shows the percentage of diabetes-free mice. (10B) The graph shows the blood glucose concentrations in PBS-treated (solid lines) or H57-597 mAb-treated (dashed lines) mice.
Figure 10B:
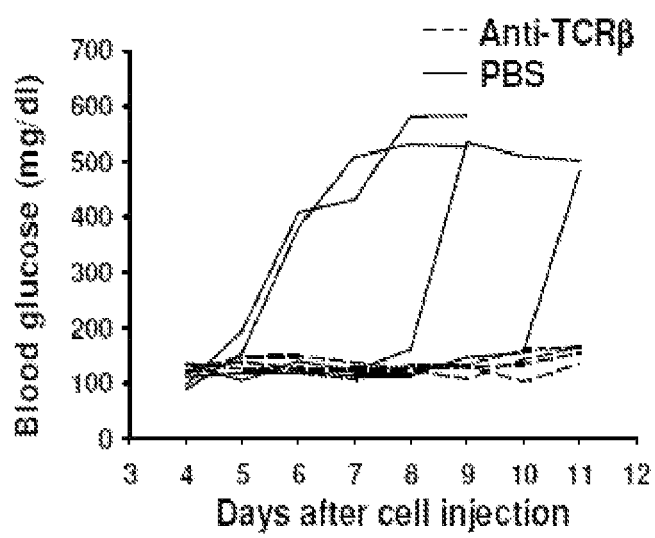
Figure 11A:
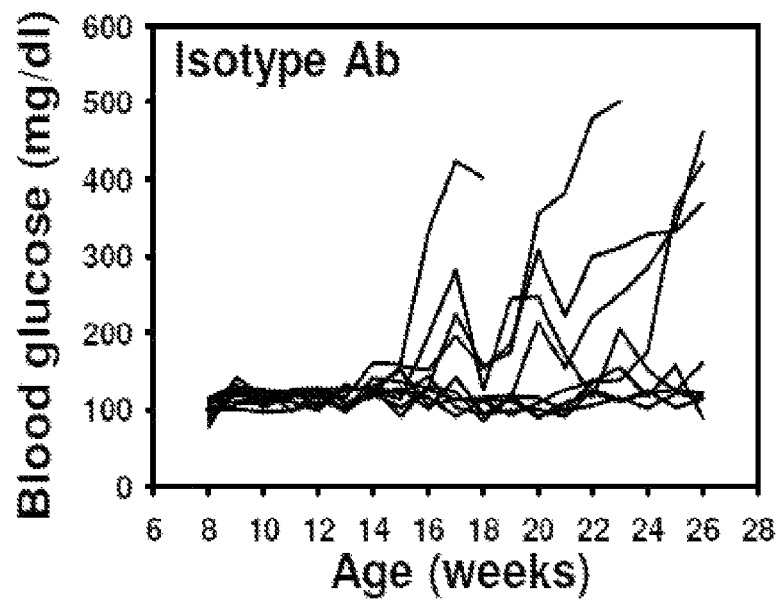
FIG. 11A-11E. A short course of H57-597 mAb prevents the development and reverses the onset of T1D in NOD mice. (11A-11D) 8-week-old female NOD mice were treated once a week for 4 weeks with anti-CD3 mAb, anti-TCR mAb, or isotype Ab. Blood glucose concentrations in isotype Ab- (11A, n=10), anti-TCR-(11B, n=10), and anti-CD3-(11C, n=8) treated mice were monitored and indicated. (11D) The graph shows the percentage of diabetes-free mice in each group. (11E) NOD mice were treated at the onset of diabetes (two consecutive blood glucose levels 250-350 mg/dL) with either isotype control Ab (right panel; n=8) or 1 mg/kg H57-597 mAb (left panel; n=8) for 10 days. The graphs show blood glucose concentrations after treatment in control vs. treated group.
Figure 11B:
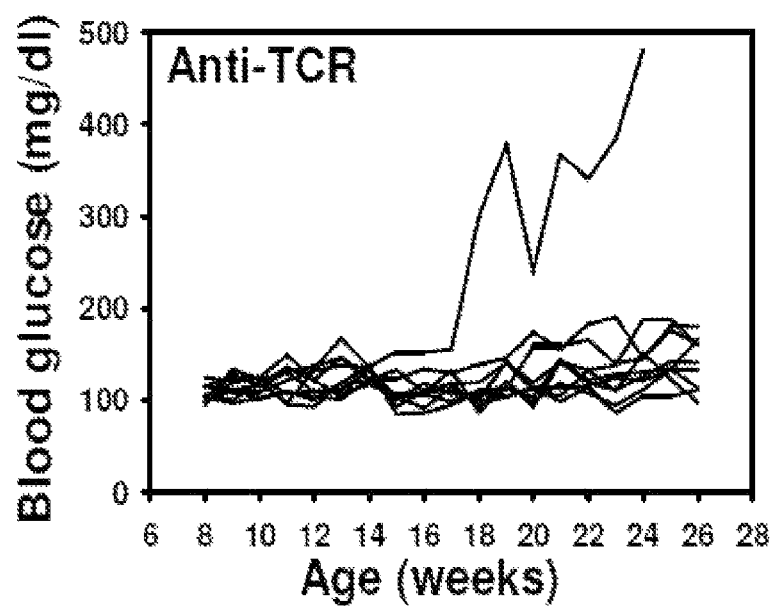
Figure 11C:
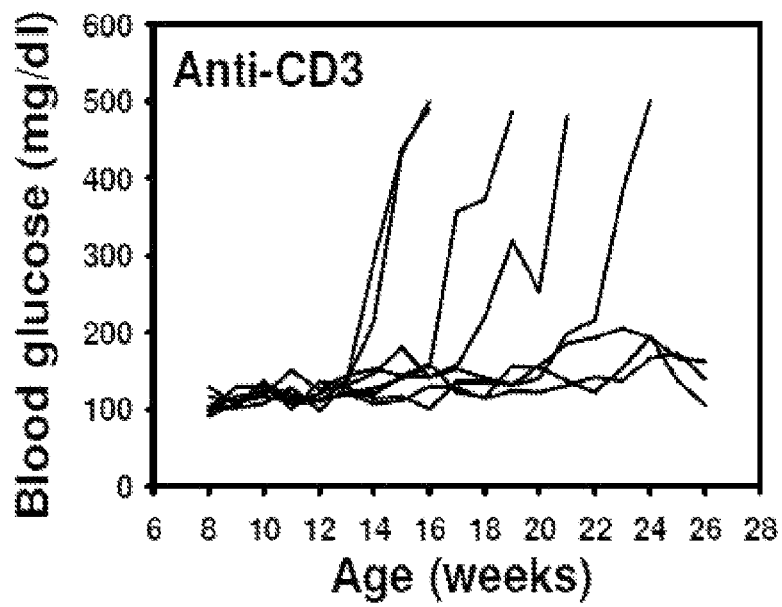
Figure 11D:
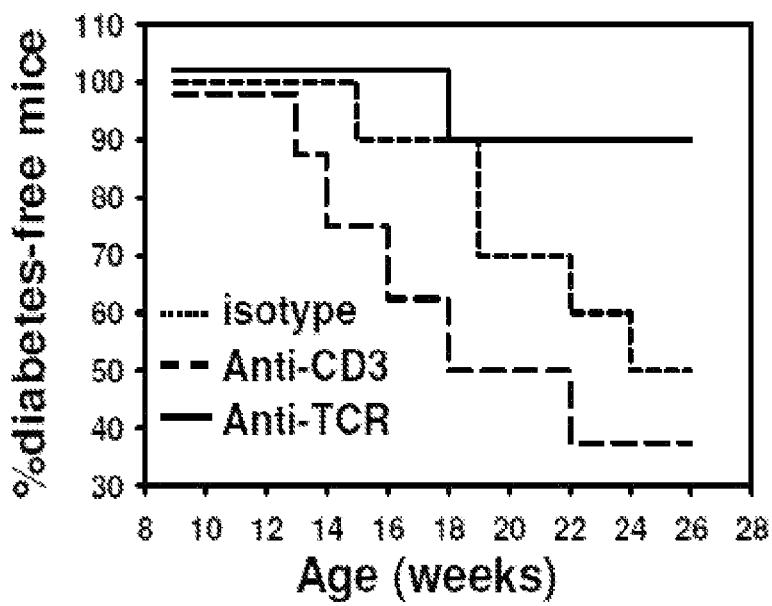

The inventors investigate the therapeutic potential of H57-597 mAb for T1D. In the "acute" T1D model, Tg RIP-OVA$^{hi}$ mice expressing OVA in the pancreatic 13 cells were adoptively transferred with OVA-specific CD8$^+$ OT-I and CD4$^+$ OT-II cells plus OVA$_{323-339}$ peptide-pulsed dendritic cells. When these RIP-OVA$^{hi}$ mice were injected with PBS, all recipients promptly developed severe diabetes within 11 days (FIGS. 10A and 10B). In contrast, a single dose of H57-597 mAb robustly inhibited diabetes in RIP-OVA$^{hi}$ mice for >250 days (FIGS. 10A and 10B). The inventors also tested the effects of H57-597 mAb on preventing T1D in NOD mice. As the majority of NOD mice spontaneously develop T1D between 12 and 26 weeks of age, the 8-week-old normoglycemic NOD mice were injected once a week for 4 weeks with 1 mg/kg anti-CD3 mAb, anti-TCR mAb, or isotype Ab control. The blood glucose monitored twice weekly showed that 5 out of 8 NOD mice developed T1D by 26 weeks of age in anti-CD3 mAb group (FIG. 11C), which was similar to 5 out of 10 NOD mice in isotype Ab group (FIG. 11A). In contrast, anti-TCR mAb prevented T1D in 9 out of 10 NOD mice (FIGS. 11B and 11D).

Figure 11E:
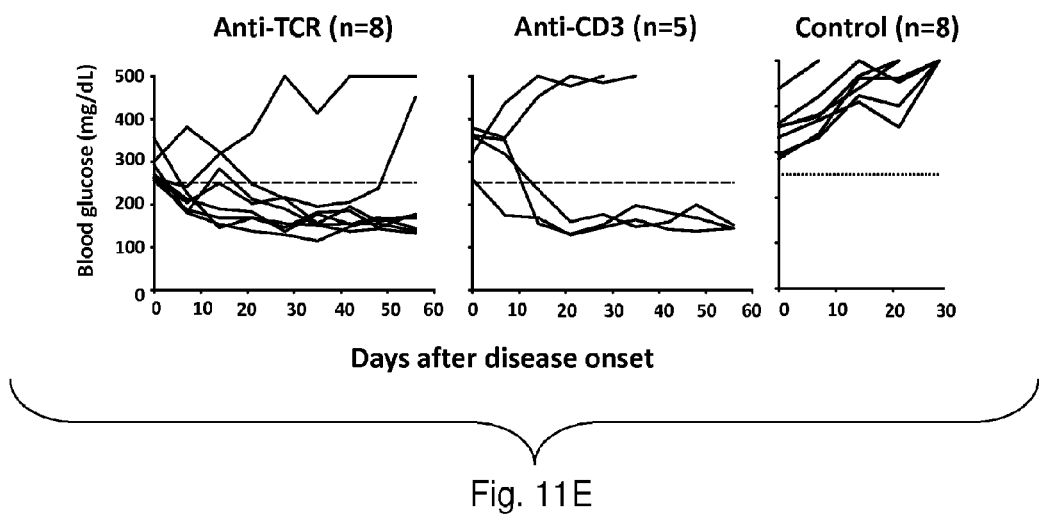

To examine whether H57-597 mAb may reverse the onset of T1D in NOD mice, immediately after T1D diagnosis (blood glucose 250-350 mg/dL) they were injected once daily for 10 days with either PBS or 1 mg/kg H57-597 mAb. While all control NOD mice developed full-blown T1D, H57-597 mAb reversed diabetes in 8 out of 8 treated NOD mice within 10 days of treatment with 6 of them remaining normoglycemic for the duration of the experiment (FIG. 11E). Therefore, transient TCR engagement with H57-597 mAb protected against and even reversed the onset of T1D.

Example 9

H57-597 mAb Exhibits Tolerogenic Effects to Heart Allografts

Figure 12A:
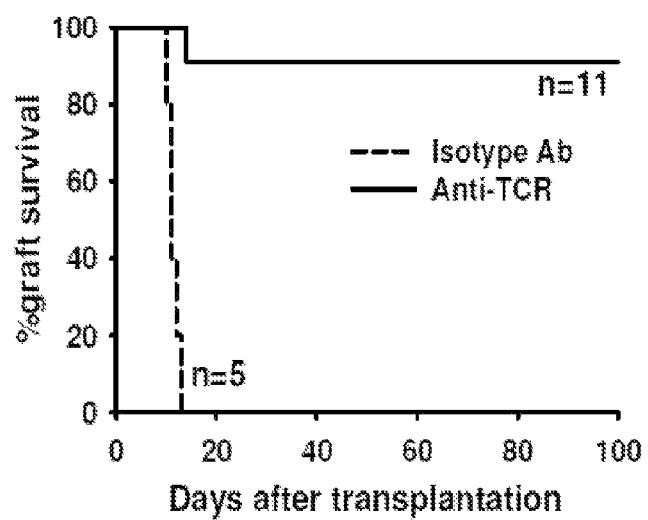
FIG. 12A-12C. Transient H57-597 mAb treatment alone displays tolerogenic effects on cardiac transplantation. (12A) B6 mice were transplanted with Balb/c heart grafts, and were injected with a short course of 1 mg/kg H57-597 mAb or its isotype Ab on day 0, 1, 3, 7 and 11 post-grafting. The graft survival was monitored by daily palpation. The graph shows the percentage graft survival after transplantation. (12B) Representative H & E stained histological sections of the heart allografts described in (A) from isotype Ab- or H57-597 mAb-treated recipients at the indicated days after transplant (top and bottom panels, respectively). (12C) B6 Rag1$^{-/-}$ mice were adoptively transferred with 3×10$^7$ splenocytes from naïve B6 mice, the above anti-TCR-treated and Balb/c graft-accepted (>100 days) B6 mice, or isotype-Ab-treated and Balb/c graft-rejected (<15 days) B6 mice. B6 Rag1$^{-/-}$ mice were then transplanted with either donor-specific Balb/c or third-party C3H hearts, the mean±SD survival of which was shown in the bar graph. * indicates p<0.01.
Figure 12B:
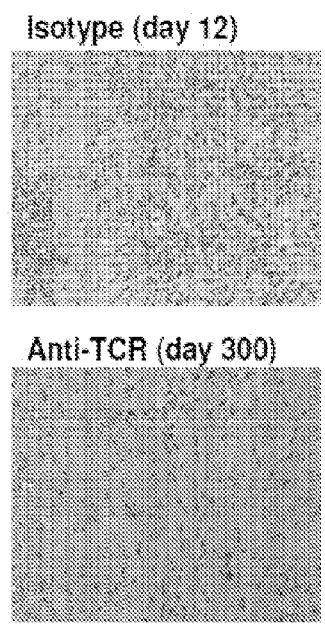

To study the tolerogenic effects of H57-597 mAb, the inventors used an MHC/non-MHC-mismatched heart transplantation model. When Balb/c (H-2d) heart allografts were transplanted into isotype Ab-treated C57BL/6 (H-2b) recipients, they all were acutely rejected within 14 days (FIG. 12A). Following H57-597 mAb therapy (1 mg/kg on days 0, 1, 3, 7 and 11 post-grafting), 10 out of 11 heart allografts remained beating at >100 days (FIG. 6A) with little graft infiltration as compared to isotype Ab-treated controls (FIG. 12B). This finding shows for the first time in a murine model that a "remodeling" of the immune response by anti-TCR mAb protected the long-term survival of heart allografts.

Figure 12C:
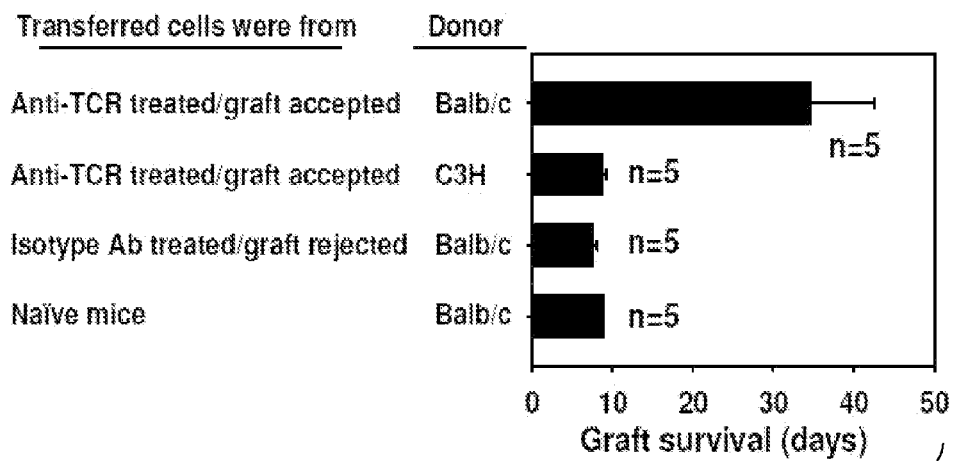

To determine the specificity of hypo-responsiveness, Rag1$^{-/-}$ mice were adoptively transferred with 3×10$^7$ splenocytes from different mice and transplanted with donor-specific Balb/c or third-party C3H (H-2$^k$) hearts. Splenocytes from Balb/c allograft-accepted recipients robustly rejected third-party C3H hearts at a mean survival time of 8.8±0.4 days, but significantly delayed the rejection of donor-specific Balb/c heart allografts at 34.6±8 days (FIG. 12C; p<0.01); Rag1$^{-/-}$ mice transferred with splenocytes from naïve B6 mice or B6 mice which rejected Balb/c heart allografts all mounted rapid rejection of Balb/c heart allografts at 9.0±0.0 days and 7.6±0.5 days, respectively (FIG. 12C). These results demonstrate that remodeling of the immune response by transient H57-597 mAb treatment exhibited long-term tolerogenic effects with donor-specific regulation.

Example 10

H57-597 mAb Combined with Anti-CD11a (LFA-1) mAb Induced Elimination of T Cells and Produced Tolerogenic Effects to Skin Allografts To test the effect of two agents in vivo, normal B6 mice were injected with 1×10$^6$ CFSE-labeled splenocytes from OTII transgenic mice and injected with 5 μg ovalbumin (OVA) peptide and 1 mg/kg H57-597 mAb and 1 mg/kg anti-CD11a mAb alone or in combination. On day 3, mice showed that 0.27% CFSE-labeled T cells in controls were reduced to 0.12% by anti-LFA-1 mAb, to 0.03% by anti-TCR mAb and to 0.00% by two agents in combination (FIG. 17). To examine the tolerogenic effects, 1 mg/kg H57-597 mAb in combination with 1 mg/kg anti-CD11a mAb were injected (days 0, 1, 3, 7 and 11 post-grafting) into B6 recipients of Balb/c skin allografts. While untreated controls rejected skin allografts within 11 days (n=3), the therapy with anti-CD11a mAb alone slightly extended survivals to maximum 14 days (n=3). In contrast, the combination therapy prolonged survivals of skin allografts to more than 30 days, and all skin grafts remain surviving (FIG. 18). These results document that anti-TCRβ mAb combined with anti-LFA-1 mAb produced complete elimination of antigen-stimulated T cells and prolonged the survivals of skin allografts.

Example 11

Therapeutic/Prophylactic Methods and Compositions

The invention provides methods of treatment and prophylaxis by administration to a subject an effective amount of a therapeutic of the present invention. In a preferred aspect, the therapeutic is substantially purified. The subject is preferably an animal, including but not limited to, animals such as cows, pigs, chickens, etc., and is preferably a mammal, and most preferably human.

Various delivery systems are known and are used to administer a therapeutic of the invention, e.g., encapsulation in liposomes, microparticles, microcapsules, expression by recombinant cells, receptor-mediated endocytosis, construction of a therapeutic nucleic acid as part of a retroviral or other vector, etc. Methods of introduction include, but are not limited to, intradermal, intramuscular, intraperitoneal, intravenous, subcutaneous, intranasal, and oral routes. The compounds are administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, the implant being of a porous, non-porous, or gelatinous material, including membranes, such as sialastic membranes, or fibers. In one embodiment, administration is by direct injection at the site (or former site) of a malignant tumor or neoplastic or pre-neoplastic tissue.

In a specific embodiment where the therapeutic includes a nucleic acid encoding a protein therapeutic the nucleic acid is administered in vivo to promote expression of its encoded protein, by constructing it as part of an appropriate nucleic acid expression vector and administering it so that it becomes intracellular, or coating with lipids or cell-surface receptors or transfecting agents, or by administering it in linkage to a homeobox-like peptide which is known to enter the nucleus. Alternatively, a nucleic acid therapeutic can be introduced intracellularly and incorporated within host cell DNA for expression, by homologous recombination.

The present invention also provides pharmaceutical compositions. Such compositions comprise a therapeutically effective amount of a therapeutic, and a pharmaceutically acceptable carrier or excipient. Such a carrier includes, but is not limited to, saline, buffered saline, dextrose, water, glycerol, ethanol, and combinations thereof. The carrier and composition can be sterile. The formulation will suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition also includes a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it is be dispensed with an infusion bottle containing sterile pharmaceutical grade water or saline. Where the composition is administered by injection, an ampoule of sterile water for injection or saline is provided so that the ingredients are mixed prior to administration.

The therapeutics of the invention are formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the therapeutic of the invention which will be effective in the treatment of a particular disorder or condition will depend on the nature of the disorder or condition, and is determined by standard clinical techniques. In addition, in vitro assays may optionally be employed to help identify optimal dosage ranges. The precise dose to be employed in the formulation will also depend on the route of administration, and the seriousness of the disease or disorder, and is decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 µg/kg body weight to 20 mg/kg body weight. Effective doses may be extrapolated from dose-response curves derived from in vitro or animal model test systems The invention also provides a pharmaceutical pack or kit comprising one or more containers filled with one or more of the ingredients of the pharmaceutical compositions of the invention. Optionally associated with such container(s) is a notice in the form prescribed by a governmental agency regulating the manufacture, use or sale of pharmaceuticals or biological products, which notice reflects approval by the agency of manufacture, use or sale for human administration.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

What is claimed is:

1. A method to make stable iTreg cells, comprising introducing an inducer composition to an inducible first cell culture,
    wherein the inducer composition comprises anti-CD3 mAb/anti-CD28 mAb and at least one composition selected from the group consisting of: anti-IL-2; antiCD25 mAb; or Janus tyrosine kinase (Jak3) inhibitor, and
    wherein the first cell culture comprises CD4$^+$Foxp3/GFP$^-$ cells in a medium with or without syngeneic antigen presenting cells.

2. The method of claim 1, wherein the inducer composition comprises anti-CD3 mAb/anti-CD28 mAb and 0 to 10 µg/ml anti-IL-2, 0 to 10 µg/ml antiCD25 mAb, and 50 to 150 nM Janus tyrosine kinase (Jak3) inhibitor.

3. The method of claim 2, wherein the inducer composition comprises: anti-CD3 mAb/anti-CD28 mAb and 5 µg/ml anti-IL-2, 5 µg/ml antiCD25 mAb, and 100 nM Janus tyrosine kinase (Jak3) inhibitor.

* * * * *

UNITED STATES PATENT AND TRADEMARK OFFICE
CERTIFICATE OF CORRECTION

PATENT NO. : 9,018,006 B2
APPLICATION NO. : 13/811778
DATED : April 28, 2015
INVENTOR(S) : Stanislaw M. Stepkowski et al.

Page 1 of 1

It is certified that error appears in the above-identified patent and that said Letters Patent is hereby corrected as shown below:

In the Specification

STATEMENT REGARDING FEDERALLY SPONSORED RESEARCH:

Column 1, Line 17, change:
"This invention was made with government support under NIH grant HL 69723, awarded by the National Institutes of Health. The government may have certain rights in this invention"

To:
--This invention was made with government support under grant number HL067923 awarded by the National Institutes of Health. The government has certain rights in the invention.--

Signed and Sealed this
Twenty-fourth Day of September, 2019

Andrei Iancu
*Director of the United States Patent and Trademark Office*

UNITED STATES PATENT AND TRADEMARK OFFICE
CERTIFICATE OF CORRECTION

PATENT NO. : 9,018,006 B2
APPLICATION NO. : 13/811778
DATED : April 28, 2015
INVENTOR(S) : Stanislaw M. Stepkowski et al.

Page 1 of 1

It is certified that error appears in the above-identified patent and that said Letters Patent is hereby corrected as shown below:

In the Specification

STATEMENT REGARDING FEDERALLY SPONSORED RESEARCH:
Column 1, Line 17, change:
"This invention was made with government support under NIH grant HL 69723, awarded by the National Institutes of Health. The government may have certain rights in this invention"
To:
--This invention was made with government support under grant number AI061052 awarded by the National Institutes of Health. The government has certain rights in the invention.--

This certificate supersedes the Certificate of Correction issued September 24, 2019.

Signed and Sealed this
Twenty-first Day of April, 2020

Andrei Iancu
*Director of the United States Patent and Trademark Office*